(12) United States Patent
Song et al.

(10) Patent No.: US 8,821,910 B2
(45) Date of Patent: *Sep. 2, 2014

(54) ALKYLAMINOALKYL OLIGOMERS AS BROAD-SPECTRUM ANTIMICROBIAL AGENT

(75) Inventors: Zhiqiang Song, Newtown, CT (US); Ted Deisenroth, Brookfield, CT (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/527,972

(22) Filed: Jun. 20, 2012

(65) Prior Publication Data

US 2012/0328683 A1    Dec. 27, 2012

Related U.S. Application Data

(60) Provisional application No. 61/500,385, filed on Jun. 23, 2011.

(51) Int. Cl.
| | | |
|---|---|---|
| *C08F 220/34* | (2006.01) | |
| *A61K 31/785* | (2006.01) | |
| *A01N 37/44* | (2006.01) | |
| *A01N 25/10* | (2006.01) | |
| *A01P 1/00* | (2006.01) | |
| *A01P 3/00* | (2006.01) | |
| *C08L 33/10* | (2006.01) | |
| *C09D 5/14* | (2006.01) | |
| *C09D 7/12* | (2006.01) | |
| *A01N 37/12* | (2006.01) | |
| *C08L 75/04* | (2006.01) | |

(52) U.S. Cl.
CPC ............ *C08F 220/34* (2013.01); *C09D 7/1233* (2013.01); *C09D 5/14* (2013.01); *A01N 37/12* (2013.01); *C08L 75/04* (2013.01)
USPC ..................... 424/411; 424/78.07; 424/78.35; 424/78.37; 523/122; 526/219.6

(58) Field of Classification Search
None
See application file for complete search history.

(56) References Cited

U.S. PATENT DOCUMENTS

| | | | |
|---|---|---|---|
| 3,592,805 A | | 7/1971 | Szabo et al. |
| 4,708,870 A | | 11/1987 | Pardini |
| 5,209,922 A | | 5/1993 | Merianos et al. |
| 5,967,714 A | | 10/1999 | Ottersbach et al. |
| 6,096,800 A | | 8/2000 | Ottersbach et al. |
| 6,790,910 B1 | | 9/2004 | Sosna et al. |
| 7,429,558 B2 | | 9/2008 | Batchelor et al. |
| 2002/0168473 A1* | | 11/2002 | Ottersbach et al. ........... 427/337 |
| 2004/0092421 A1 | | 5/2004 | Ottersbach et al. |
| 2006/0127644 A1 | | 6/2006 | Nun et al. |
| 2010/0197829 A1 | | 8/2010 | Obrecht |

FOREIGN PATENT DOCUMENTS

| | | |
|---|---|---|
| EP | 0204312 | 12/1986 |
| KR | 101021960 | 3/2001 |

OTHER PUBLICATIONS

Sandrine Lenoir, Christophe Pagnoulle, Moreno Galleni, Philippe Compere, Robert Jerome, and Christophe Detrembleur. Polyolefin Matrixes with Permanent Antibacterial Activity: Preparation, Antibacterial Activity, and Action Mode of the Active Species. Biomacromolecules 2006, 7, 2291-2296.*

Krzysztof Matyjaszewski and Jianhui Xia. Atom Transfer Radical Polymerization. Chem. Rev. 2001, 101, 2921-2990.*

International Search Report dated Mar. 29, 2013.

* cited by examiner

*Primary Examiner* — Frederick Krass
*Assistant Examiner* — Michael P Cohen
(74) *Attorney, Agent, or Firm* — Shiela A. Loggins

(57) ABSTRACT

The present application relates to oligomeric antimicrobial compounds and compositions comprising the same. The oligomers are formed by polymerizing aminoalkyl(meth)acrylate or aminoalkyl(meth)acrylamide monomer(s). In addition to imparting materials with broad spectrum antimicrobial activity, the oligomers can impart antimicrobial activity to substrates such as hair and skin.

17 Claims, 1 Drawing Sheet

Optical microscopy photograph (100x) of the PVC films containing 5% low Mw pTBAEMA (7A) and high Mw pTBAEMA (7B).

Photograph of the TPU plaques containing 2% pTBAEMA (8A) with different Mw

ALKYLAMINOALKYL OLIGOMERS AS BROAD-SPECTRUM ANTIMICROBIAL AGENT

This application claims benefit under 35 USC 119(e) of U.S. provisional application No. 61/500,385, filed Jun. 23, 2011 and herein incorporated entirely by reference.

TECHNICAL FIELD

The present application relates to compositions comprising a material or substrate treated with or containing oligomers formed by polymerizing aminoalkyl(meth)acrylate or aminoalkyl(meth)acrylamide monomer(s). The materials are for example, coatings, inks, adhesives, lubricants, textiles, membranes, polymers, plastics, rubbers, waxes, metals, glass, ceramics, wood or cellulosic substrates, gels, paper, pharmaceuticals, packaging materials, home and personal care formulations and cosmetics. The oligomers impart broad-spectrum antimicrobial protection to the materials including antifungal properties. Accordingly, this application describes not only the oligomers and method of preparing them but also the process for imparting antimicrobial activity to the various materials. Silicone rubber, PVC and TPU materials are of particular interest. In addition to imparting materials with broad spectrum antimicrobial activity, the oligomers can impart antimicrobial activity to substrates such as hair, skin and wounds.

BACKGROUND

Bacterial and fungal fouling is known to cause damage or lead to contamination of surfaces such as of medical devices, hospital theatres, teeth and kitchen surfaces, swimming pools, industrial pipes, architectural structures, and ships hulls. Such contamination can lead to microbial infection and remains one of the most serious problems associated with biomaterials. Patients using medical devices and appliances ranging from orthopedic pins, plates and cardiac implants through to wound dressings and urinary catheters must constantly guard against bacteria infection. It is also known that the number of invasive fungal infections is steadily increasing world wide. Therefore there continues to exist a strong need for improved antimicrobials which provide effectiveness against not only bacterial contamination but also fungal contamination and which are easily incorporated within or onto materials including biomaterials to provide the needed antimicrobial effect whilst causing little or no adverse effect on the physical properties of the material such as appearance, strength and impact resistance.

The use of particular polymers as antimicrobial agents is known in the art. Further it is known that polymers of tert-butylaminoethyl methacrylate (tBAEMA) have antimicrobial activity.

For example, European Application No. 0204312 discloses non-fugitive antimicrobial activity of acrylic copolymers with aminoalkyl(meth)acrylic monomers including dimethylaminoethyl methacrylate (DMAEMA), diethylaminoethyl methacrylate (DEAEMA) and tertiarybutylaminoethymethacrylate in protonated form.

U.S. Pat. No. 5,209,922 discloses an antifungal block copolymer of vinyl lactam with quaternized aminoalkyl acrylamide.

U.S. Pat. No. 3,592,805 discloses preparation of fungicidal compounds obtained by complexing perhalogenated acetone derivatives with amine compounds including tBAEMA.

U.S. Pat. No. 5,967,714 discloses antimicrobial polymers prepared by graft copolymerization of tert-butylaminoethyl methacrylate with one or more aliphatically unsaturated monomers on plastic substrates. U.S. Pat. No. 6,096,800 discloses a process for the preparation of antimicrobial plastics by carrying out polymerization of t-butylaminoethyl methacrylate (tBAEMA) in the presence of plastic articles.

U.S. Pat. No. 6,790,910 discloses water-insoluble homopolymers of aminoalkyl methacrylates such as tBAEMA and DEAEMA having antimicrobial activity.

The above references however have certain disadvantages. For example, the high molecular weight aminoakylmethacrylate polymers described above are not easily incorporated into materials, especially polymeric materials. High molecular weight polymers are generally quite viscous and thus may require solubilization by solvents before incorporation onto or into a material. Grafting of the polymer onto a material requires an additional grafting step. While grafting may impart antimicrobial activity and prevent leaching, the grafting step may otherwise adversely impact the physical properties of the grafted material.

While the references above teach that polymers of aminoalkyl methacrylates have antimicrobial imparting effects against bacteria, the above polymers fail to provide as effective antifungal protection against multicellular mold fungi, especially on *Aspergillus niger*.

SUMMARY OF THE INVENTION

The inventors have discovered that many of the above difficulties can be resolved by using oligomers of poly aminoalkyl(meth)acrylates or poly aminoalkyl(meth)acrylamides. The inventors have determined that low molecular weight polymers (oligomers) are more easily incorporated within and on to materials or substrates. For example, they may easily be incorporated as a melt blend into thermoplastic substrates. In particular, the oligomeric polyaminoalkyl (meth)acrylates or oligomeric polyaminoalkyl(meth)acrylamides are easy to incorporate into or on polymers, such as silicone rubber, polyvinylchloride (PVC) and thermoplastic polyurethanes (TPU). This is unexpected in that silicones or silicone rubbers are nonpolar while the polyaminoalkyl (meth)acrylates or polyaminoalkyl(meth)acrylamides are relatively polar and yet the inventive oligomers can be incorporated at relatively high levels.

Furthermore, the oligomers are appreciably soluble in common polar solvents such as ethanol and methanol. This gives a processing advantage in that the oligomers may be applied easily to a surface or substrate while in solution without special aids for homogenous application such as surfactants.

Additionally, even though oligomers are of low molecular weight once incorporated into a polymer, the oligomers do not leach into the surrounding environment. This non-leaching is important not only for maintaining the antimicrobial properties of the composition or substrate, for example in moist environs, but also leaching of low molecular weight additives from any biomaterial used in human environs is considered highly disadvantageous.

Additionally and most unexpectedly, the present oligomers provide antimicrobial protection not only against bacteria (gram positive and gram negative) and yeast but also is unexpectedly more effective than higher molecular weight similar polymers against fungi. Furthermore, the oligomers are also more efficient requiring lower loading.

The present application is therefore directed to a composition containing the oligomer formed from formula (I) as defined below, a process of imparting antimicrobial properties to said materials or substrates, and the use of the antimicrobial oligomer to impart antimicrobial and odor reducing effects to said materials.

The composition is an antimicrobial composition comprising a material selected from the group consisting of coatings, ink, adhesives, lubricants, textiles, polymers, plastics, superabsorbers, rubbers, waxes, metals, ceramics, glass, wood or cellulosic substrates, membranes, gels, paper, pharmaceuticals, water, home and personal care formulations, packaging material and cosmetics which material is treated with or incorporates an antimicrobial oligomer formed from a monomer of formula (I)

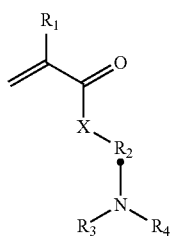

(I)

wherein $R_1$ is H or $CH_3$,
$R_2$ is $C_1$-$C_5$ alkyl bi-radical,
$R_3$ and $R_4$ are independently H or $C_1$-$C_5$ alkyl radical which can be linear or branched, and X is a divalent radical of —O—, —NH— or —$NR_5$, wherein $R_5$ is $C_1$-$C_6$ alkyl and the oligomer has a weight average molecular weight (Mw) of 400 to 20,000 g/mole, preferably the weight average molecular weight (Mw) ranges from 400 to 10,000 g/mole and optionally with a polydispersity index between 1 and 4.0, preferably between 1 and 3.0 (determined according to GPC calibrated with poly methyl methacrylate narrow molecular weight standards).

It is preferred that if the material is a polymer, the polymer polyvinyl acetate is excluded.

A process of imparting antimicrobial and odor reducing properties to a material comprising the steps of incorporating into or treating the material with the oligomer formed from the monomer of formula (I) above, and the material is selected from the group consisting of coatings, inks, adhesives, lubricants, gels, textiles, membranes, polymer, plastics, rubbers, metal, ceramics, glass waxes, wood or cellulosic substrates, paper, pharmaceuticals, water, home or personal care formulations, packaging material and cosmetics.

Use of an oligomer formed from
a monomer of formula (I)

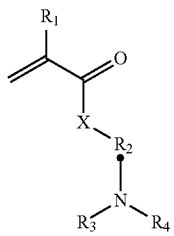

(I)

wherein $R_1$ is H or $CH_3$,
$R_2$ is $C_1$-$C_5$ alkyl bi-radical,
$R_3$ and $R_4$ are independently H or $C_1$-$C_5$ alkyl radical which can be linear or branched, and X is a divalent radical of —O—, —NH— or —$NR_5$, wherein $R_5$ is $C_1$-$C_6$ alkyl and the oligomer has an weight average molecular weight (Mw) of 400 to 20,000 g/mole, preferably the weight average molecular weight (Mw) ranges from 400 to 10,000 g/mole, optionally, with a polydispersity index between 1 and 4.0, preferably between 1 and 3.0 (determined according to GPC calibrated with poly methyl methacrylate narrow molecular weight standards), to impart antimicrobial and odor reducing properties to substrates is also envisioned.

DETAILED DESCRIPTION OF THE INVENTION

Oligomer

Figure 1:
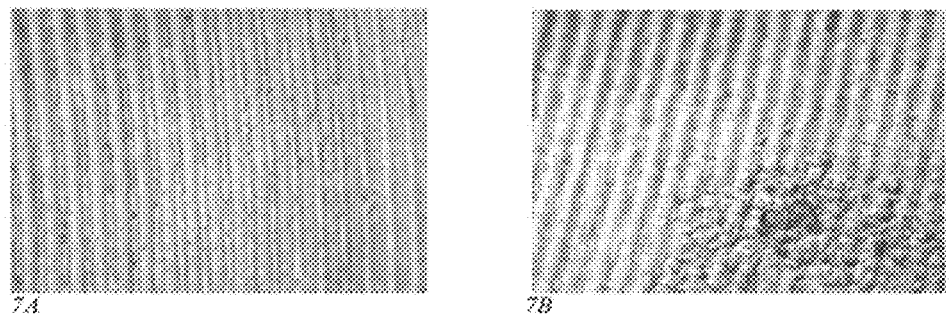
FIG. 1 shows a microscopy photograph (100×) of the PVC films containing 5 wt. % low $M_w$ pTBAEMA (7A) and 5 wt. % high $M_w$ pTBAEMA (7B). See example 7.

Oligomer for purposes of this application means a repeating unit ranging from 2 to 100, preferably from 5 to 60, and most preferably from 10 to 40. Depending upon the formula weight of the repeat unit this will translate into a weight average molecular weight ($M_w$) between 400 to 20,000 g/mole or a number average molecular weight ($M_r$) of from 400 to 10,000 g/mole.

Molecular Weight

Low molecular weight and oligomer are synonymous or exchangeable terms for purposes of this application. However, when the term molecular weight is used this will normally indicate a weight average molecular weight ($M_w$) unless otherwise indicated.

Degree of Polymerization

Degree of polymerization means the number of repeat monomer units making up a polymer. For example, if the degree of polymerization is 100, then 100 monomer units are incorporated into the polymer.

Comprising

Comprising for purposes of the invention is open ended, that is other components may be included. Comprising is synonymous with containing or including.

Filler

Fillers are primarily inorganic and may be crystalline or amorphous.

The fillers are often used in polymers to impart certain properties such as fire retardncy, and antiblocking properties. Filler may be selected from the group consisting of silica, silicates including alkali/aluminum silicates, carbonates such as magnesium or calcium carbonates or dolomite, kaolin, mica, metal oxides or metal hydroxides, carbon black, graphite, carbon fibres or wiskers, ceramic fibres or wiskers, zinc borate, alumina trihydrate, calcium silicate or magnesium silicate, wollastonite, barium sulfate, barium titanate, barium ferrite and precursors thereof, preferably silica, silicates, metal oxides, barium sulfate and precursors thereof, most preferably metal oxides (ie. titanium oxide), silica and silicates.

Broad-Spectrum Antimicrobial Effect

For purposes of this application, broad-spectrum antimicrobial effect means an effect against pathogenic gram negative, gram positive bacteria, viruses, yeast, fungi and mold and against bacteria of the skin and scalp flora, including such organisms as those responsible for dandruff and acne.

(Meth)acrylate means methacrylate or acrylate and likewise (meth)acrylamide means methacrylamide or acrylamide.

Water-Insoluble

The low molecular weight antimicrobial oligomers are substantially water-insoluble. The term substantially "water-insoluble" for purposes of this application means that less than 5 wt. %, preferably less than 3 wt. %, most preferably less than 1 wt. % and especially 0.5 or 0.1 wt. %, most especially <100 ppm or <10 ppm of the oligomer is soluble in deionized water at room temperature (25° C.) and pressure. For example, the antimicrobial oligomer according to formula (II) may be <10 ppm soluble in deionized water at room temperature.

The Oligomers

The term "the oligomers" in the context of this application means, the antimicrobial oligomers.

The antimicrobial oligomers are made by polymerizing an alkylaminoalkyl(meth)acrylate or an alkylaminoalkyl(meth)acrylamide monomer in a way to achieve low molecular weight.

Suitable alkylaminoalkyl(meth)acrylate and alkylaminoalkyl(meth)acrylamide monomers may be represented by general formula (I):

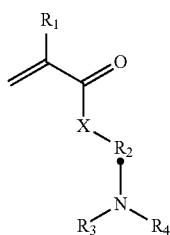

(I)

wherein
R$_1$ is H or CH$_3$,
R$_2$ is C$_1$-C$_5$alkyl bi-radical,
R$_3$ and R$_4$ are independently H or C$_1$-C$_5$alkyl radical which can be linear or branched,
and X is a divalent radical of —O—, —NH— or —NR$_5$, wherein R$_5$ is C$_1$-C$_6$ alkyl.

Preferred monomers from formula (I) are 2-tert-butylaminoethyl(meth)acrylate (tBAEMA), 2-dimethylaminoethyl(meth)acrylate, 2-diethylaminoethyl(meth)acrylate, 3-dimethylaminopropyl(meth)acrylate, N-3-dimethylaminopropyl(meth)acrylamide, and N-3-diethylaminopropyl(meth)acrylamide with the most preferred being 2-tert-butylaminoethyl(meth)acrylate (tBAEMA).

The oligomers may be formed from a monomer meeting the description of formula (I) only or may be formed from additional monomers. For example, the oligomer may be formed from one or more monomers of formula (I) selected from the group consisting of -tert-butylaminoethyl(meth)acrylate (tBAEMA), 2-dimethylaminoethyl(meth)acrylate, 2-diethylaminoethyl(meth)acrylate, 3-dimethylaminopropyl(meth)acrylate, N-3-dimethylaminopropyl(meth)acrylamide, and N-3-diethylaminopropyl(meth)acrylamide. Alternatively, the oligomer may be formed from the monomers of formula (I) and additional monomers not meeting the definition of formula (I).

However, preferably the oligomer is formed only from monomers meeting the definition of formula (I). While the oligomer may be a co-oligomer it is preferable that the oligomer is a homo-oligomer.

It is most preferably that the oligomer is a homo-oligomer and formed from tBAEMA only.

The most preferred oligomers of the present invention are obtained from t-butylaminoethyl methacrylate (tBAEMA) and are represented by formula (II).

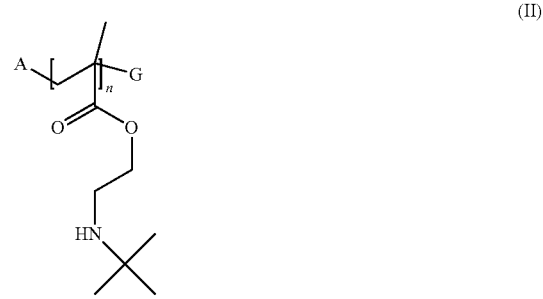

(II)

where n is from 2 to 100, and A and G are residual groups derived from initiator and optionally a chain transfer agent used in polymerization. Preferably n is from 5 to 60, and most preferably from 10 to 40.

n represents the degree of polymerization.

A and G are derived from initiators and optionally chain transfer agents. The polymerization initiators may be selected from the group consisting of free radical polymerization initiators, atom transfer radical polymerization (ATRP) initiators, nitroxide-mediated radical polymerization (NMP) initiators, reversible addition-fragmentation chain transfer polymerization (RAFT) or macromolecular design via interchange of xanthates (MADIX), preferably atom transfer radical polymerization (ATRP).

Preferably the polymerization initiator is a free radical polymerization initiator with A and G being derived from the residual group of initiators selected from the group consisting of azo and peroxide initiators and optionally a chain transfer agent.

It is also possible that the initiators are atom transfer radical polymerization initiators (ATRP) and in this case A and G will be derived from alkyl halide initiator. Thus, A may be an alkyl 2-isobutyrate radical and G a halide which can be obtained by using an alkyl 2-haloisobutyrate ATRP initiator. Most especially in the case of ATRP, G is a bromide or an iodide, which may presumably contribute to enhance antifungal activity of the antimicrobial oligomers of the present invention.

The molecular weights of oligomers formed from formula (I) and represented by formula (II) are measured by gel permeation chromatography (GPC) using poly(methyl methacrylate) narrow molecular weight standards. The oligomers may be of a weight average molecular weight (Mw) ranging from 400 to 20,000 g/mole, preferably from 1000 to 10,000.

Most preferably the weight average molecular weight (M$_w$) of the oligomers ranges from 400 to 20,000 g/mole and a number average molecular weight (M$_r$) from 400 to 10,000 g/mole.

In particular, oligomers of pTBAEMA having a M$_w$=<20K are characterized by a T$_g$ of =<30° C. preferably=<25° C. Accordingly, the T$_g$ of the polymer formed from a monomer of formula (I) or an oligomer of formula (II) has a T$_g$ of =<30° C., preferably =<25° C. or less.

The oligomers formed from formula (I) or oligomers of formula (II) preferably have a narrow molecular weight distribution with a polydispersity index ranging from (PDI=$M_w$/$M_n$) of 1.0 to 4.0, preferably 1.0 to 3.0.

Most preferably, the oligomers formed from formula (I) or oligomers of formula (II) have $M_w$ ranging from 1000 to 10,000 with a PDI ranging from 1.0 to 2.0.

The oligomers formed from formula (I) may have virtually any architecture, that is they may be grafted, linear, block, star, hyper-branched, random or brush architecture. Preferably, the architecture of formula (I) is linear or block, and most preferably the architecture of formula (I) is linear.

The oligomers can be crosslinked or non-crosslinked but preferably the oligomers are non-crosslinked.

The weight contribution of A and G will normally be higher than typical medium and high molecular weight polymers of formula (II) as high concentrations of initiators favor low molecular weight polymers. Thus the oligomers of formula (II) will on the average be shorter chains with A+G (the terminating groups formed from the initiator) making a larger weight percent contribution to the oligomer.

The molar contribution of A+G can be expressed as a ratio of A+G to degree of polymerization n of the monomer or as mole percent of the oligomer. As the degree of polymerization decreases the molar percent contribution of A+G increases.

For example, if the degree of polymerization of the oligomer ranges from n=2 to 100, then the molar contribution of A+G (sum of A and G) will range from 1:2 to 1:100. For n ranging from 5 to 60, then the molar contribution of A+G will range from 1:5 to 1:60. For n ranging from 10 to 40, the molar contribution of A+G will range from 1:10 to 1:40.

Accordingly the mole % of A+G based on the total moles of initiator terminal groups and moles of monomer units (degree of polymerization n) for n=2 to 100, n=5 to 60 and n=10 to 40 would range from about 1 to about 30, preferably about 1.5 to about 17, most preferably about 2.4 to about 9 mole percent respectively.

Alternatively this could be expressed in weight percent contribution of the A and G residual groups. This of course will depend on the molecular weight of A and G however the weight contribution of the A and G residual groups would normally range from about 0.5 to about 40 wt. %, preferably about 0.5 to about 35 wt. %, most preferably about 0.5 to about 5 wt. %.

Thus the antimicrobial and antifungal oligomer of formula (II) may be preferably defined as

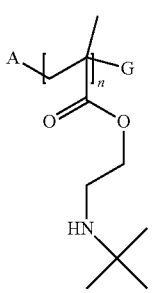

(II)

where n is from 2 to 100, preferably n is from 5 to 60, and most preferably from 10 to 40. and A and G are residual groups derived from an initiator and optionally a chain transfer agent used in polymerization,
wherein the mole percent of A+G ranges from about 1 to about 30, preferably about 1.5 to about 17, most preferably about 2.4 to about 9 mole percent based on the total moles of A+G and monomer units and the initiator is selected from the group consisting of free radical polymerization initiators, atom transfer radical polymerization (ATRP) initiators, nitroxide-mediated radical polymerization (NMP) initiators, reversible addition-fragmentation chain transfer polymerization (RAFT) or macromolecular design via interchange of xanthates (MADIX), preferably atom transfer radical polymerization (ATRP), preferably the initiator is a free radical initiator selected from the group consisting of azo and peroxide initiators.

Preparation of the Oligomers

The broad-spectrum antimicrobial alkylaminoalkyl oligomers of the present invention can be prepared by conventional random radical polymerization, controlled radical polymerization (CRP), anionic polymerization and cationic polymerization with reaction conditions aimed for low molecular weight polymers. The preparation of the oligomers can be carried out using various polymerization techniques such as solution, emulsion, microemulsion, inverse emulsion, and/or bulk polymerizations, as well as other technologies that are available to those who are skilled in the art.

The free radical polymerization is preferably carried out in solution or in bulk using azo or peroxide compounds as radical initiator.

Molecular weights of polymers synthesized by radical polymerization, anionic polymerization and cationic polymerization can be controlled by varying reaction conditions such as initiator type and concentration, monomer concentration, reaction temperature, chain transfer agent type and concentration. Generally, high concentration of initiator, low concentration of monomer, high reaction temperature and addition of a chain transfer agent are used to achieve low molecular weights for the broad-spectrum antimicrobial oligomers.

Conventional random radical polymerization provides a simple way to make the oligomers. The source of free radicals required to initiate the polymerization of the radically polymerizable monomers is a free radical initiator. The free radicals may be formed by thermal or photoinduced decomposition of the initiator or by a redox reaction with the initiator.

Typical free radical initiators include, but are not limited to azo and peroxide compounds.

Typical azo initiators include azobis(isobutyronitrile) (AIBN), dimethyl 2,2'-azobisisobutyrate (MAIB), 1,1'-azobis(1-cylcohexanenitrile), 2,2'-azobis(2,4,4-trimethylpentane), and azobis-2,4-dimethylvaleronitrile, polymeric or oligomeric materials comprising azo, —N=N—, groups. Water soluble azo initiator may be used in emulsion polymerization and selected from the group consisting of 2,2-azobis-(N,N'-dimethylene-isobutyramidine)dihydrochloride, 2,2'-azobis-(2-amidinopropane)dihydrochloride, 4,4'-azobis-(4-cyanopentane-carboxylic acid); 2,2'-Azobis[2-(5-methyl-2-imidazolin-2-yl)propane]dihydrochloride; 2,2'-Azobis[N-(2-carboxyethyl)-2-methylpropionamidine]tetrahydrate; 2,2'-Azobis[2-(3,4,5,6-tetrahydropyrimidin-2-yl)propane] dihydrochloride; and 2,2'-Azobis{2-methyl-N-[2-(1-hydroxybuthyl)]propionamide.

Typical peroxide radical initiator may include acyl and diacyl peroxides, alkyl peroxides, dialkyl peroxydicarbonates, hydroperoxides such as tert.-butylhydroperoxide, peresters, and inorganic peroxides such as hydrogen peroxide, ammonium persulfate, potassium persulfate and sodium persulfate, benzoyl peroxide (BPO) or a peroxy acid such as peroxyacetic acid or peroxybenzoic acid. The redox initiator in combination with reducing agents is selected from the group consisting of, for example, an acyl peroxides with tertairyamine such as triethylamine, and tert.-butylhyderoperoxide or persulfate with iron(II)-ammonium sulfate, ascorbic acid, sodium methyl sulfinate, disodium disulfite, sodium hydrogen sulfite, sodium phosphite, potassium phosphate, hydrogen phosphite, sodium hypophosphite or potassium hypophosphite.

Azo initiators such as AIBN is preferably used at high concentration from 1% to 20% based on monomer to achieve low molecular weight using radical polymerization to prepare the antimicrobial oligomers. Lower concentration of initiator may be used in combination with an effective chain transfer agent to obtain low molecular weight.

Suitable chain transfer agents may include mercaptans such as dodecyl mercaptan, octyl mercaptan, hexyl mercaptan and ethanolmercaptan and halogen-containing compounds such as carbon tetrabromide.

Controlled living polymerization methods may be used for preparing the antimicrobial oligomers. Living polymerization techniques have been traditionally used for the synthesis of well-defined polymers where polymerization proceeds in the absence of irreversible chain transfer and chain termination, i.e. nearly ideally in anionic polymerization and less ideally in cationic polymerization. Anionic living polymerization is initiated by nucleophilic addition to the double bond of the monomer using an organo-metallic initiator such as an alkyl lithium or Grignard reagent. An alternative means of initiation is electron transfer which occurs when alkali metals or similar species as the initiators. Cationic polymerization, on the other hand, is initiated by electrophilic agents such as a protonic acid and a Lewis acid. Examples of Lewis acid initiators include $AlCl_3$, $SnCl_4$, $BF_3$, $TiCl_4$, $AgClO_4$, and $I_2$ in combination with a co-initiator such as $H_2O$ or an organic halogen compound.

Although most of the ionic living polymerization techniques are not tolerant towards primary and secondary amino functional groups in the monomers to be polymerized, anionic polymerization of t-butylaminoethyl methacrylate is possible because of its relative low basicity. The low MW antimicrobial tBAEMA oligomers of the present invention can be prepared by anionic polymerization method described in "Living anionic homo- and block copolymerization of 2-(tert-butylamino)ethyl methacrylate" by Serge Creutz, Philippe Teyssie and Robert Jerome, J. Polymer Science (part A), vol 35 (10), 1997, 2035-2040 using a monomer to initiator molar ratio of from 5 to 100. Preferred initiators are diphenylmethyllithium with lithium chloride.

Controlled radical polymerizations are also suitable to prepare the antimicrobial oligomers. Controlled radical polymerization is provided by recent methods such as atom transfer radical polymerization (ATRP), nitroxide-mediated radical polymerization (NMP), reversible addition-fragmentation chain transfer polymerization (RAFT) and other related processes involving a degenerative transfer, such as macromolecular design via interchange of xanthates (hereinafter referred as MADIX).

ATRP is one of the envisioned polymerization methods to make the low $M_w$ antimicrobial oligomers which provide broad-spectrum antimicrobial activity. See *Langmuir* 2006, 22(1), 255-262.

ATRP is normally initiated by the redox reaction between an initiator comprising a transferable atom or group and catalyst comprising a transition metal complex in a lower oxidation state. The transferable atom or group (G) can be homolytically cleaved from the initiator by the catalyst, thereby oxidizing the catalyst to a high oxidation state and forming a radical thereby activating the initiator residual (A) for monomer addition. After the initiation, the ATRP process is mediated by the catalyst in a fast dynamic equilibrium between activating and deactivating the polymer chains via a similar homolytic atom or group transfer through the redox reaction.

Any transition metal complex capable of maintaining the dynamic equilibrium with the polymer chain may be used as the redox catalyst in ATRP. Suitable catalysts may be transition metal complexes of copper, ruthenium, iron, rhodium, nickel and palladium, molybdenum, and osmium. Preferred transition metal catalysts are copper complexes such as copper (I) halides with a ligand. The metal catalyst can be reduced form (e.g., Cu+), in oxide form (e.g., Cu+2), in atom form (e.g. Cu(0)) or mixture of all the metal forms in different valence. A particular ATRP process called "single electron transfer" (SET) living radical polymerization (LRP) uses only metal copper (Cu(0)) as initial catalyst, but the other valence forms of copper (Cu+ and Cu+2) are also generated in-situ and present during the polymerization process. In the so called reverse ATRP process, only metal in oxide form (e.g., Cu+2) is added initially, but metal in the reduced form (Cu+) is generated in-situ to make atom transfer radical polymerization work.

Suitable ligands for ATRP catalyst include but are not limit to bipyridine compounds, polydentate amines, terpyridyl and quadridentate amine bearing pyridine. Examples of pyridine compounds are 2,2'-bipyridine, 4,4' substituted 2,2'-bipyridine (such as 4,4'-di(5-nonyl)-2,2'-bipyridine and 4,4'-diheptyl-2,2'-bipyridine), BIS(2-PYRIDINAL)ETHYLENEDIIMINE, tris-(2-pyridylmethyl)amine (TPMA). Examples of dentate amine ligands are hexa-N,N-substituted tris[2-(amino)ethyl]amine (TREN) such as tris[2-(N,N-dimethylamino)ethyl]amine (Me6TREN), 1,1,4,7,10,10-hexamethyltriethylenetetramine (HMTEA), and penta methyl diethylene triamine (Me5DETA). Preferred ligands for ATRP catalyst are Me6TREN, TPMA, and HMTEA. Tetradentated branched ligands such as Me6TREN and TPMA form highly active catalysts with copper halids such as CuBr and are the most suitable for the preparation of low MW antimicrobial tBAEMA oligomers at low temperature and low degrees of polymerization.

Suitable ATRP initiators include, but not limited to, halogenated alkanes, benzylic halides, α-haloesters, α-haloketones, alkyl and aryl sulfonyl chlorides. Preferred initiators are α-haloesters and α-haloketones, More preferred initiators are α-haloesters such as 2-haloisobutyrates and 2-halobutyrates. Examples of α-haloester initiators are ethyl 2-bromoisobutyrate (EBiB) and ethyl 2-bromobutyrate.

The preferred ATRP initiators may be represented by formula III

where G is the transferable atom or group which may be homolytically cleaved from the initiator by the catalyst for ATRP process and E is an alkyl or a functional group which, desirably, may impart antifungal activity in addition to the antimicrobial activity originated from the tBAEMA main oligomer chain. Example functional groups for E may include haloalkyl such as bromoethyl, hydroxyalkyl such as hydroxyethyl, halobenzyl such as bromobenzyl, and propargyl, a polyene radical with multicinjugated double bonds and group containing imidazole, triazole, or thiazole entities which are known to have antifungal activity.

When low $M_w$ antimicrobial tBAEMA oligomer represented by formula II is obtained by ATRP using an initiator from formula II, the A group may be represented by formula (IV).

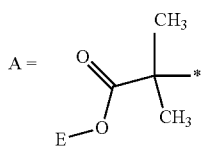

While not limiting the scope of the invention, it is believed that the added antifungal activity against multicellular microorganism of the tBAEMA oligomers appears to result from low molecular size. Reduced molecular size of the tBAEMA oligomer may make the antimicrobial agent easier to penetrate and/or attach to multicellular structure of mold fungi for killing. Homopolymers of tBAEMA has been previously shown to act as an antimicrobial peptide mimic with facially amphiphilic structure. See G. J. Gabriel et al., *Materials Science and Engineering R* 57 (2007), page 28-64 and C. J. Hewitt et al., *Biotechnology Letters* 26: pages 549-557, 2004.

The oligomeric broad-spectrum antimicrobial agent may be made by ATRP process using a halo-initiator such as α-haloesters and a-haloketones. More preferred ATRP initiator is selected from α-bromoesters such as 2-bromoisobutyrates and α-iodoesters such as 2-iodoisobutyrates.

When the antimicrobial oligomers are made by the ATRP process, the initiator to monomer ratio may range from to 0.001 to 1, preferably from 0.01 to 0.5, and more preferably from 0.02 to 0.2 by mole.

The ratio of transition metal to the initiator may range from 0.01 to 1. The reaction temperature may range from 0 to 200° C. and preferably from 20 to 100° C.

The antimicrobial oligomer may be combined with other known antimicrobial agents. For example, the oligomeric antimicrobial may be combined with diphenyl ethers such as Triclosan® or Diclosan® registered trademarks of BASF Corporation.

Other antimicrobial active substances which may be combined with the inventive antimicrobial oligomer include phenol derivatives, benzyl alcohols, chlorhexidine, $C_{12}$-$C_{14}$ alkylbetaines, $C_8$-$C_{18}$ fatty acid amido alkyl-betaines, amphoteric surfactants, trihalocarbanilides and quaternary ammonium salts. Silver containing antimicrobials are also envisioned such as those under the tradenames Irgaguard® and Hygentic® also available from BASF Corporation.

Application Using Oligomers in and on Materials and Substrates

As explained above the antimicrobial and antifungal oligomers may be incorporated in or on a diverse range of materials thus providing antimicrobial protection. The materials broadly include coatings, ink, adhesives, lubricants, textiles, polymers, plastics, rubbers, waxes, wood or cellulosic substrates, metals, ceramics, glass, membranes, gels, superabsorbers, paper, pharmaceuticals, water (such as cooling towers, water tanks etc.), home and personal care formulations, packaging materials and cosmetics.

The antimicrobial oligomers are also useful for disinfection, deodorization and for general and antimicrobial treatment of the skin (including scalp) and mucosa and of integumentary appendages (hair), for example, for the disinfection of hands, skin, hair and wounds.

The antimicrobial oligomers are suitable on both animal and human skin or scalp.

The antimicrobial oligomers are also suitable as preservatives.

Home and Personal Care Applications

For example, the antimicrobial oligomers are suitable as antimicrobial active substances and preservatives in personal care preparations. For example, personal care preparations include shampoos, bath additives, hair care preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleaning cloths, oils or powders.

The antimicrobial oligomers are also suitable for cosmetic formulations. There come into consideration, for example, the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams or oils, sun-blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

The following represent examples of various formulations containing the antimicrobial oligomers of the invention. Obviously, these are simple, basic formulations only and a wide variety of similar formulations are known in the art into which the present antimicrobial oligomers at various concentrations are readily incorporated.

An antimicrobial soap has, for example, the following composition:
0.01 to 5% by weight of antimicrobial oligomer,
0.3 to 1% by weight titanium dioxide,
1 to 10% by weight stearic acid,
soap base ad 100%, e.g. a sodium salt of tallow fatty acid or coconut fatty acid, or glycerol.

A shampoo has, for example, the following composition:
0.01 to 5% by weight of antimicrobial oligomer,
12.0% by weight sodium laureth-2-sulfate,
4.0% by weight cocamidopropyl betaine,
3.0% by weight NaCl and
water ad 100%.

A deodorant has, for example, the following composition:
0.01 to 5% by weight antimicrobial oligomer,
60% by weight ethanol,
0.3% by weight perfume oil, and
water ad 100%.

The invention relates also to an oral composition containing from 0.01 to 15% by weight, based on the total weight of the composition, of the antimicrobial oligomer, and orally tolerable adjuvants.

Example of an oral composition:
10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of antimicrobial oligomer, and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name OLAFLUOR.

It is further possible that the antimicrobial oligomers may be used as a preservative, that is protect the above personal care compositions from microbial damage during storage. When used in this capacity, the antimicrobial oligomers are added at concentrations ranging from 5 to 10000 ppm.

Accordingly, this disclosure encompasses a method of preserving personal care and home care formulations from the deleterious action of microbial contamination by adding to said formulations the antimicrobial oligomer defined by formula (I) or formula (II) in concentrations ranging from about 5 to about 10000 parts per million, where the parts per million are based on the total weight of the formulation.

The antimicrobial oligomers of this invention are also used in washing and cleaning formulations, e.g. in liquid or powder washing agents or softeners.

The antimicrobial oligomers can also be used in household and general-purpose cleaners for cleaning and disinfecting hard surfaces.

A cleaning preparation has, for example the following composition:
0.01 to 5% by weight antimicrobial oligomers
3.0% by weight octyl alcohol 4EO
1.3% by weight fatty alcohol $C_8$-$C_{10}$polyglucoside
3.0% by weight isopropanol
water ad 100%.

The compounds according to the invention are also suitable for the protection of cosmetic products and household products from microbial damage.

The antimicrobial oligomers may be part of a polish, such a furniture polish, or a dispersant or surfactant formulation such as a glycol or mineral oil dispersion or other formulation as used in for example wood protection.

Textiles

In addition to preserving cosmetic and household products, the preservation of technical products, the provision of technical products with antimicrobial properties and use as a bio-cide in technical processes are also possible, for example in paper treatment, especially in paper treatment liquors, printing thickeners of starch or cellulose derivatives, surface-coatings and paints.

The antimicrobial oligomers of the invention are also suitable for the antimicrobial treatment of wood and for the antimicrobial treatment of leather, the preserving of leather and the provision of leather with antimicrobial properties.

The antimicrobial oligomers of this invention are also suitable for treating, especially preserving, textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose.

Paper, for example papers used for hygiene purposes, may also be provided with antimi-crobial properties using the antimicrobial oligomers of this invention.

It is also possible for nonwovens, e.g. nappies/diapers, sanitary towels, panty liners, and cloths for hygiene and household uses, to be provided with antimicrobial properties in accordance with the invention. These hygiene articles may further comprise superabsorbers.

When the material is a textile and the textile is likely in the form of a gauze, bandage, wound dressing, film dressing and adhesive plaster pads, supporters, sheets, wipers, wipes, surgical drape, superabsorbents, or surgical clothing.

The oligomer may be directly applied to the textile or incorporated therein. For example, the oligomer may be incorporated into nonwoven substrate by treating with a solution or dispersion containing the oligomer. Alternatively, the oligomer may be incorporated via a melt blending into the fibers used to form the nonwoven.

Textiles would include among others, a protective article worn by patients, healthcare workers, or other persons who may come in contact with potentially infectious agents or microbes, including an article of clothing such as a gown, robe, face mask, head cover, shoe cover, or glove; alternatively, the protective article may include a surgical drape, surgical fenestration or cover, drape, sheets, bedclothes or linens, padding, gauze dressing, wipe, wet wipes, sponge and other antimicrobial articles for household, institutional, health care and industrial applications. In certain embodiments, the article contains the composite only on one surface, for example the surface of a face mask which will face away from the body and possibly be exposed to pathogens. Non-woven substrates are in particular envisioned.

The non-woven substrate material is normally a multi layered material. For example, an outer or inner fabric may be layered to another sheet ply, e.g., a filter or barrier media. In many embodiments, not all of the other layers need to be treated with the antimicrobial composite. In one particular embodiment, only one layer of a layered polyolefin fabric is treated with the antimicrobial composite. For example, a SMS polypropylene fabrics which comprise a spunbond polypropylene layer on each face of a meltbound polypropylene layer are common in protective garments such as face masks and other disposable garments used in hospital settings. Often, only the surface of the fabric that faces away from the body, and exposed to contamination, is treated with an antimicrobial composite. One embodiment of the invention relates to the treatment of only the "outer layer" of such materials and articles.

It is further possible to incorporate the antimicrobial oligomer into the fibers themselves of the non-woven.

The textile may for example be a natural or synthetic textile. Treatment of natural cellulose fibres, such as cotton, linen, jute and hemp, as well as cellulose and regenerated cellulose is envisioned wherein the oligomer is applied directly to the textile surface or the fibers are pre-treated with the antimicrobial oligomer before the fabric is woven.

The antimicrobial oligomer may also be added to such substrates as gels which may be used in combination with the above textile. Additionally the antimicrobial oligomer may be used directly in gels which are used in wound healing compositions.

Superabsorbers

Furthermore, the antimicrobial oligomer may be used in or on a hygiene article as mentioned above suitable for the absorption of urine, menses, and/or feces. These hydgiene article may further contain superabsorbers.

Examples of such articles would include for example, baby-diapers, absorbent pads, incontinence articles and tampons. Such articles are effective in absorbing liquids especially when treated with superabsorbers.

Superabsorbents are known. Superabsorbents are materials that are able to take up and retain several times their weight in water, possibly up to several hundred times their weight, even under moderate pressure. Such materials are also commonly known by designations such as "high-swellability polymer", "hydrogel" (often even used for the dry form), "hydrogel-forming polymer", "water-absorbing polymer", "absorbent gel-forming material", "swellable resin", "water-absorbing resin" or the like. The materials in question are crosslinked hydrophilic polymers, in particular polymers formed from (co)polymerized hydrophilic monomers, graft (co)polymers of one or more hydrophilic monomers on a suitable grafting base, crosslinked ethers of cellulose or starch, crosslinked carboxymethylcellulose, partially crosslinked polyalkylene oxide or natural products that are swellable in aqueous fluids, examples being guar derivatives, of which water-absorbing polymers based on partially neutralized acrylic acid are most widely used.

The manufacture of superabsorber material (SAP) is well known and described for example in: *Modern Superabsorbent Technology*, Wiley VCH, 1998, Editors Fredric L. Buchholz & Andrew T. Graham The superabsorber itself may be treated, coated or admixed with the antimicrobial oligomer. This combination of the superabsorber with antimicrobial oligomer, may reduce odor formation caused by anti-microbial decomposition of the body exudates. In particular, the formation of ammonia odor may be prevented due to the anti-microbial effect of the inventive resin.

Hygiene articles normally comprise fibers, non-wovens, films, and may further comprise superabsorbent materials. Fibers can be made for example of cellulose, chemically or thermally modified cellulose, polyesters, cellulose acetate, polypropylene and other synthetic resins. Mixtures of fibers can be used.

Accordingly, a method of controlling odor or interfering with ammonia formation caused by anti-microbial decomposition of body exudate is envisioned by combining a superabsorber polymer with the antimicrobial oligomer of formula (I) or formula (II) for example when exposed to the body exudate.

The antimicrobial oligomer may simply be coated onto the superabsorbent polymer or admixed with the superabsorbent material which in turn may be coated onto a hygiene article.

Hygiene articles with the side facing the users body may be coated with the antimicrobial oligomer. This enables direct contact of the antimicrobial on the skin of the wearer.

Plastics and Coatings

The antimicrobial oligomers of this invention are suitable also for treating, especially imparting antimicrobial properties to or preserving, plastics, e.g. polyethylene, polypropylene, polyurethane, polyester, polyamide, polycarbonate, latex etc. Fields of use therefore are, for example, floor coverings, plastics coatings, plastics containers and packaging materials; kitchen and bathroom utensils (e.g. brushes, shower curtains, sponges, bathmats), latex, filter materials (air and water filters), plastics articles used in the field of medicine, e.g. dressing materials, syringes, catheters etc., so-called "medical devices", gloves and mattresses.

The antimicrobial oligomers of this invention are suitable also for treating, especially imparting antimicrobial properties to or preserving industrial formulations such as coatings, lubricants etc. The preservative concentrations within the formulations, coatings or lubricants may range from 5 to 10000 parts per million wherein the parts per million are based on the total weight of the formulation.

Anti-microbial coatings may include coatings such as architectural coatings but also include applications in medical devices used in consumer healthcare and personal hygiene products as well as in biomedical/biotechnical laboratory equipment.

When applied as a part of a film or coating, the antimicrobial compounds may also comprises a binder.

The binder may be any polymer or oligomer compatible with the present antimicrobials. The binder may be in the form of a polymer or oligomer prior to preparation of the anti-fouling composition, or may form by polymerization during or after preparation, including after application to the substrate. In certain applications, such as certain coating applications, it will be desirable to crosslink the oligomer or polymer of the anti fouling composition after application.

The term binder as used in the present invention also includes materials such as glycols, oils, waxes and surfactants commercially used in the care of wood, plastic, glass and other surfaces. Examples include water proofing materials for wood, vinyl protectants, protective waxes and the like.

The composition may be a coating or a film. When the composition is a thermoplastic film which is applied to a surface, for example, by the use of an adhesive or by melt applications including calendaring and co-extrusion, the binder is the thermoplastic polymer matrix used to prepare the film.

When the composition is a coating, it may be applied as a liquid solution or suspension, a paste, gel, oil or the coating composition may be a solid, for example a powder coating which is subsequently cured by heat, UV light or other method.

As the composition of the invention may be a coating or a film, the binder can be comprised of any polymer used in coating formulations or film preparation. For example, the binder is a thermoset, thermoplastic, elastomeric, inherently crosslinked or crosslinked polymer.

Thermoset, thermoplastic, elastomeric, inherently crosslinked or crosslinked polymers include polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, silicon containing and carbamate polymers, fluorinated polymers, crosslinkable acrylic resins derived from substituted acrylic esters, e.g. from epoxy acrylates, urethane acrylates or polyester acrylates. The polymers may also be blends and copolymers of the preceding chemistries.

Biocompatible coating polymers, such as, poly[-alkoxyalkanoate-co-3-hydroxyalkenoate] (PHAE) polyesters, Geiger et. al. Polymer Bulletin 52, 65-70 (2004), can also serve as binders in the present invention.

Alkyd resins, polyesters, polyurethanes, epoxy resins, silicone containing polymers, polyacrylates, polyacrylamides, fluorinated polymers and polymers of vinyl acetate, vinyl alcohol and vinyl amine are non-limiting examples of common coating binders useful in the present invention. Other coating binders, of course, are part of the present invention.

Coatings are frequently crosslinked with, for example, melamine resins, urea resins, isocyanates, isocyanurates, polyisocyanates, epoxy resins, anhydrides, poly acids and amines, with or without accelerators.

The compositions of present invention are for example a coating applied to a surface which is exposed to conditions favorable for bioaccumulation. The presence of the antimicrobial compounds of this invention in said coating will prevent the adherence of organisms to the surface.

The anti-microbial compounds of the present invention may be part of a complete coating or paint formulation, such as a marine gel-coat, shellac, varnish, lacquer or paint, or the anti fouling composition may comprise only a polymer of the instant invention and binder, or a polymer of the instant invention, binder and a carrier substance. It is anticipated that other additives encountered in such coating formulations or applications will find optional use in the present applications as well.

The coating may be solvent borne or aqueous. Aqueous coatings are typically considered more environmentally friendly.

The coating is, for example, aqueous dispersion of a polymer of the instant invention and a binder or a water based coating or paint. For example, the coating comprises an aqueous dispersion of a polymer of the instant invention and an acrylic, methacrylic or acrylamide polymers or co-polymers or a poly[-alkoxyalkanoate-co-3-hydroxyalkenoate]polyester.

The coating may be applied to a surface which has already been coated, such as a protective coating, a clear coat or a protective wax applied over a previously coated article.

Coating systems include marine coatings, wood coatings, other coatings for metals and coatings over plastics and ceramics. Exemplary of marine coatings are gel coats comprising an unsaturated polyester, a styrene and a catalyst.

The coating is, for example a house paint, or other decorative or protective paint. It may be a paint or other coating that is applied to cement, concrete or other masonry article. The coating may be a water proofer as for a basement or foundation.

The coating composition is applied to a surface by any conventional means including spin coating, dip coating, spray coating, draw down, or by brush, roller or other applicator. A drying or curing period will typically be needed.

Coating or film thickness will vary depending on application and will become apparent to one skilled in the art after limited testing.

The composition may be in the form of a protective laminate film.

Such a film typically comprises thermoset, thermoplastic, elastomeric, or crosslinked polymers. Examples of such polymers include, but are not limited to, polyolefin, polyimide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, fluorinated polymers, silicon containing and carbamate polymers. The polymers may also be blends and copolymers of the preceding chemistries.

When the anti-fouling composition is a preformed film it is applied to the surface by, for example, the use of an adhesive, or co-extruded onto the surface. It may also be mechanically affixed via fasteners which may require the use of a sealant or caulk wherein the esters of the instant invention may also be advantageously employed.

A plastic film may also be applied with heat which includes calendaring, melt applications and shrink wrapping.

The amount of the antimicrobial oligomers which may be added to for example, coatings to achieve an antimicrobial effect, may range from 0.01% to 20%, preferably from 0.1% to 10% by weight, wherein the percent is based on the total weight of the coating.

It is further possible to prepare polymer concentrates or masterbatches of the antimicrobial oligomers. This is possible by combining the oligomer with a suitable polymer under melt conditions in a heatable container such as a kneader, mixer or extruder. The loading of the antimicrobial oligomers in the concentrate is for example about 10 to 60 weight percent of the total composition. The masterbatch or antimicrobial oligomer concentrates can then easily be incorporated into plastic injection molded articles and synthetic fibers.

Biomaterials

The oligomeric antimicrobial agent may be beneficially incorporated in, and migrate to the surface of, biomaterials such as plastics for biomedical devices to impart antimicrobial and anti-biofilm forming properties on surface.

Examples of biomaterials for medical devices are silicone rubbers used for catheters, polyolefins such as polyethelene (PE) used for pharmaceutical bottle, catheter, nonwoven fabric, pouch, and orthopedic implants, and polypropylene (PP) used for disposable syringes, blood oxygenator membrane, suture, nonwaven fabric, and artificial vascular grafts, polyvinylchloride (PVC) used for blood and solution bag, surgical packging, intravenous injection sets, dialysis devices, catheter bottles, connectors and cannulae, polymethylmethacrylate (MMA) used for blood pump and reservoirs, membrane for blood dializer, implantable ocular lens and bone cement, styrene polymers used for tissue culture wares, roller bottles, vacuum canister, filterwares, clamps, blood dialyzers, diagnostic test kits, polyesters such as polyethylenterephthalate (PET) used for implantable suture, mesh, artificial vascular grafts and heart valve, polytetrafluoroethylene (PTFE) used for catheter and artificial vascular grafts, polyamides (Nylon) used for packaging film, catheters, sutures and mold parts, natural rubbers used for fabrication of implants, polyacetal and polysulfone used for implant materials, and polycarbonate used for food packaging.

The preferred plastics or polymers for biomaterials are selected from the group consisting of polysiloxane, silicon rubber, polyolefins, polyvinylchloride, polymethylmethacrylate, polyesters, polytetrafluoroethylene, polyamides, natural rubbers, polyacetal, polysulfones, polyurethanes, thermoplastic polyurethanes (TPU), polyethers and polycarbonates.

Most preferred plastics or polymers for biomaterials are selected from the group consisting of thermal plastic urethanes (TPU), thermoplastic polyolefins (PTO), thermoplastic elastomers (TPE) and silicone rubbers.

Silicone rubber is an especially important material for bio-applications. Accordingly, one of the objectives of the present invention is to provide a method of incorporating the oligomer in liquid silicone rubber (LSR) and formation of an antimicrobial silicone rubber.

Liquid silicone rubber (LSR) are usually two packages of liquid silicone materials of different compositions. The two parts individually have long enough shelf-life and are stable and remain liquid until they are mixed together. When the two packages of the liquid silicone materials are mixed together, crosslinking takes place and the mixture will cure and form solid elastomeric material at an appropriate temperature.

The mixing of two different polymers of high MW tends to induce phase separation largely due to un-favorable mixing entropy. The incompatibility of high MW polymer become more pronounced involving mixing two polymers of very different types. Non polar Silicone rubber is normally incompatible with polar polymers such as amino polymers. Beside the compatibility issue, the catalyst used in liquid silicone rubber formulation for curing could be easily affected by presence of reactive amine functionality from the amino polymer.

Figure 2:
FIG. 2 shows a photograph of the TPU plaques containing 2% pTBAEMA (8A) with different M. See example 9.

As indicated in FIGS. 1 and 2, compatibility of the oligomeric antimicrobial is much better than that of the higher Mw materials. Clarity of transparent resins (FIG. 2) and overall appearance (FIG. 1) is much improved with the oligomer antimicrobial.

Accordingly, this application is also directed to a process of forming an antimicrobial and antifungal silicone rubber composition, comprising the steps of i.) adding the oligomer formed from a monomer of formula (I)

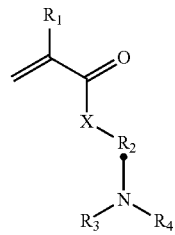

wherein $R_1$ is H or $CH_3$,
$R_2$ is $C_1$-$C_5$ alkyl bi-radical,
$R_3$ and $R_4$ are independently H or $C_1$-$C_5$ alkyl radical which can be linear or branched, and X is a divalent radical of —O—, —NH— or —$NR_5$—, wherein $R_5$ is $C_1$-$C_6$ alkyl and the oligomer has an average molecular weight (Mw) of 400 to 20,000 g/mole, preferably the average molecular weight (Mw) ranges from 400 to 10,000 g/mole and optionally with a polydispersity index between 1 and 3.0 (determined according to GPC calibrated with poly methyl methacrylate narrow molecular weight standards),
to a silicone rubber composition which composition comprises
  a polysiloxane,
  optionally a crosslinker and/or filler,
  and
  a catalyst,
ii.) and curing.

Unexpectedly, the present oligomers are highly compatible within the liquid silicone systems, i.e. there is little to no phase separation upon combining and they do not interfere with the crosslinking reaction even at relatively high concentrations. Furthermore, they do not leach from the substrate and while providing the needed effective antimicrobial activity.

Additionally, the present oligomers are more effective than high molecular weight polyalkylamino(meth)acrylates or (meth)acrylamides. Lower concentrations of the oligomers achieve the same effective antimicrobial activity.

The oligomeric antimicrobial agent may be applied by itself or in a formulation with other ingredients into or onto various materials to impart biocidal and anti-biofilm activity. Examples of suitable material as mentioned above include coatings, inks, adhesives, lubricants, textiles, polymers, plastics or rubbers, superabsorbers, membranes (for example in the prevention of biofouling in desalination plants), gels, waxes, ceramics, metal, glass, wood or cellulosice substrates, paper, water systems (for example to prevent biofouling), pharmaceuticals, packaging materials cosmetics and home or personal care formulations.

Bioflims

In addition to their generally antimicrobial action, the antimicrobial oligomers are capable of penetrating biofilms on living and non-living surfaces, of preventing the adhesion of bacteria to surfaces and any further build-up of the biofilm, of detaching such biofilm and/or inhibiting the further growth of the biofilm-forming micro-organisms in the biological matrix, or of killing such micro-organisms.

Biofilms are understood, very generally, to be aggregations of living and dead micro-organisms, especially bacteria, that adhere to living and non-living surfaces, together with their metabolites in the form of extracellular polymeric substances (EPS matrix), e.g. polysaccharides. The activity of antimicrobial substances that normally exhibit a pronounced growth-inhibiting or lethal action with respect to planktonic cells may be greatly reduced with respect to microorganisms that are organized in biofilms, for example because of inadequate penetration of the active substance into the biological matrix.

This may relate to biofilms on human or animal tooth surfaces and oral mucosa, which play a crucial role in the onset of degenerative diseases in the oral cavity, e.g. caries or periodontitis, as a result of the biofilm-forming micro-organisms or their metabolites.

Action against bio-films in the present invention also relates to biofilms on non-human surfaces. US Published Patent Application 20070128151 discloses compounds useful in coatings or films in protecting surfaces from bio-fouling. Such surfaces include surfaces in contact with marine environments (including fresh water, brackish water and salt water environments), for example, the hulls of ships, surfaces of docks or the inside of pipes in circulating or pass-through water systems. Other surfaces are susceptible to similar bio-fouling, for example walls exposed to rain water, walls of showers, roofs, gutters, pool areas, saunas, floors and walls exposed to damp environs such as basements or garages and even the housing of tools and outdoor furniture.

The antimicrobial compounds of this invention are also useful in preventing bio-fouling, or eliminating or controlling microbe accumulation on the surfaces described in US Published Patent Application 20070128151 either by incorporating the antimicrobial compounds into the article or surface of the article in question or by applying the antimicrobial to these surfaces as part of a coating or film as described in US Published Patent Application 20070128151.

When the anti-fouling composition is a preformed film it is applied to the surface by, for example, the use of an adhesive, or co-extruded onto the surface. It may also be mechanically affixed via fasteners which may require the use of a sealant or caulk wherein the antimicrobial oligomers of the instant invention may also be advantageously employed.

Molds and fungi are especially problematic for calks and sealants, causing dark unattractive discoloration. The present antimicrobial oligomer is particularily appropriate as a protectant against their invasion and accompanying discoloration.

Water Systems

The oligomeric antimicrobial agents can be used to protect against microorganism contamination in solutions, dispersions such as water systems (cooling towers, water tanks, desalination plants etc.) to eliminate biofouling and on surfaces such as those of medical devices, hospital theatres, teeth and kitchen and bathroom surfaces, swimming pools, industrial pipes, architectural structures, membranes and ships hulls.

Thus the oligomeric antimicrobial agents may be incorporated into or onto various materials to impart broad-spectrum antimicrobial activity. The material may be organic or inorganic materials.

Preferably the materials are selected from the group consisting of coatings, inks, adhesives, lubricants, textiles, polymers, rubbers, plastics, membranes, gels, metals, ceramics, waxes, wood or cellulosic substrates, paper, pharmaceuticals, home and personal care formulations, packaging materials (especially food packaging materials), superabsorbers and cosmetics.

The amount of the antimicrobial oligomers present in or on the coating, inks, adhesives, lubricants, textiles, polymers or plastics, membranes, gels, waxes, ceramics, metals, glass, wood or cellulosic substrates, paper, water, pharmaceuticals, home and personal care formulations, packaging materials and cosmetics compositions may range form 0.01% to 100%, preferably from 1% to 20% by weight, wherein the weight is based on the total weight of the composition.

Further, the incorporation of the antimicrobial oligomers into or on a packaging components such as a film, coating, container or label is envisioned, especially for food packaging.

The antimicrobial oligomer may be melt blended with the polymeric packaging component or alternatively the antimicrobial oligomers may be used to coat the packaging material.

Particular embodiments of the invention therefore relate to

The effective amount of antimicrobial oligomer for purposes of the embodiments unless otherwise specified below means the oligomers may be added at concentrations varying from about 0.001 to about 20 wt %, preferably 0.001 to 10 wt. %, most preferably 0.001 to 5 wt %, wherein the wt. % is based on the total weight of the plastics, coatings, other materials of construction, home or personal care formulations or industrial formulations.

Methods for protecting plastics, coatings, other materials of construction, home or personal care formulations, industrial formulations or technical process against the action of microbes which comprises adding an effective amount of the anti-microbial compounds of the present invention;

Methods for protecting skin, mucosa and integumentary appendages against the action of microbes including protecting the scalp from dandruff or skin from acne, which comprises applying a preparation comprising an effective amount of the anti-microbial compounds of the present invention to the skin, mucosa or integumentary appendages;

In particular, a method for protecting the scalp against dandruff comprises applying a personal care formulation comprising an effective amount of the anti-microbial oligomers of formula (I) or formula (II) to the scalp. The effective amount of the antimicrobial oligomer within the personal care formulation ranges from about 0.001 to about 2 wt. %.

Methods for protecting paper, wood, leather, synthetic textile materials or natural textile materials such as cotton against the action of microbes comprising incorporating or applying an effective amount of the present polymer or copolymer or a composition comprising an effective amount the anti-microbial compounds of the present invention;

Methods for cleaning and disinfecting hard surfaces which comprises applying a preparation comprising an effective amount of the anti-microbial compounds of the present invention;

Methods for preventing bio-fouling of an article comprising incorporating anti-microbial compounds of the present invention into the article or surface of the article or by applying the anti-microbial compounds of the present invention to these surfaces either directly or as part of a coating or film.

Methods of protecting packaging materials (labels, trays, plastics for wrapping, bags etc.), especially food packaging materials or packaging for medical devices, against the action of microbes comprising incorporating or applying an effective amount of the present oligomer in or on the packaging material.

Methods of protecting membranes or air filters against the action of microbes and fungi comprising incorporating an effective amount of the present oligomer into or onto said membrane or filter.

Hygiene articles suitable for the absorption of urine, menses, and/or feces comprising the antimicrobial oligomer formed from the monomer according to formula (I) or the antimicrobial oligomer according to formula (II) and a superabsorber.

Use of superabsorbers in combination with the antimicrobial oligomer formed from the monomer according to formula (I) or the antimicrobial oligomer according to formula (II) for the purpose of elimination of order from the decomposition of body exudates.

A treatment for forming a superabsorber capable of reducing odors or reducing ammonia production by combining the superabsorber with the antimicrobial oligomer formed from the monomer according to formula (I) or the antimicrobial oligomer according to formula (II).

Methods of controlling odor caused by anti-microbial decomposition of body exudate comprising the step of combining a superabsorber polymer and the antimicrobial oligomer formed from the monomer of formula (I) or the oligomer of formula (II) and exposing said combination to the body exudate.

Methods of preserving personal care and home care formulations from the deleterious action of microbial or fungal contamination by adding to said formulations the antimicrobial oligomer formed by the monomer defined by formula (I) or the oligomer of formula (II) in concentrations ranging from about 5 to about 10000 parts per million, where the parts per million are based on the total weight of the formulation.

Methods of preventing bio-fouling of water systems comprising the addition of an effective amount of the antimicrobial oligomer formed from the monomer of formula (I) or the oligomer of formula (II) to said water system.

The water system may for example be a cooling tower, a desalination plant or a water tank.

Other materials of construction include, in addition to wood, metals, paper, glass, ceramics, coatings, plastics and textiles, materials such as concrete, cement, adhesives, caulking materials, composites of natural and synthetic materials etc.

The following examples describe certain embodiments of this invention, but the invention is not limited thereto. It should be understood that numerous changes to the disclosed embodiments can be made in accordance with the disclosure herein without departing from the spirit or scope of the invention. These examples are therefore not meant to limit the scope of the invention. Rather, the scope of the invention is to be determined only by the appended claims and their equivalents.

EXAMPLES

Example 1

Synthesis of tBAEMA oligomers via ATRP

Into a 50 mL three neck round bottom flask reactor are charged 0.1549 g (0.1 mMole) of CuBr, 0.075 g (0.02 mMole) of $CuBr_2$, 0.342 g of tris[2-(dimethylamino)ethyl]amine ($Me_6TREN$) and 5.50 g of dimethyl sulfoxide (DMSO). The reactor content is mixed and sparged with nitrogen for about 10 minutes. At the same time, 18.28 g (0.1 mole) of t-butylaminoethyl methacrylate (tBAEMA) and 1.93 g (0.01 mole) Ethyl 2-bromoisobutyrate (EBiB) are mixed and sparged with nitrogen in a drop funnel for 10 minutes. The reactant content in the drop funnel is added to the reactor under nitrogen sparging to start polymerization. After polymerization under nitrogen for about 2 hours, the reactor content is precipitated in 300 mL of hexane and stirred overnight. The residual catalysts are removed from bottom DMSO phase and the polymer is recovered from the hexane phase through rotary evaporation. The polymer is re-dissolved in 10 g of DMSO and precipitated in fresh boiling hexane again to further remove residual monomer and catalysts. The polymer was recovered again by rotary evaporation and then dried in a vacuum oven at 50° C. overnight. The purified polymer product is analyzed with gel permeation chromatography (GPC) to have a number average molecular weight (Mn) of 2,700 and a weight average molecular weight (Mw) of 4,500 using poly(methyl methacrylate)monodisperse molecular weight standards from Polymer Labs. The molecular weight polydispersity index (PDI=Mw/Mn) is 1.67.

Comparison Example A

Preparation of tBAEMA Polymer

Following the procedure described in Example 1 of U.S. Pat. No. 6,096,800 using azobisisobutyronitrile (AIBN) initiator and tetrahydrofuran (THF) solvent, a tBAEMA homopolymer was prepared and characterized by GPC to have a weight average molecular weight (Mw) of 174,000 and a number average molecular weight of 63,000 (polydispersity index Mw/Mn=2.75).

Comparison Example B

Preparation of tBAEMA Polymer

Following the same procedure of Comparison Example 1 except double the amount of the THF solvent to low the initial monomer concentration, a lower MW tBAEMA homopolymer was prepared and characterized by GPC to have a weight average molecular weight (Mw) of 91,000 a number average molecular weight of 12,000 (polydispersity index Mw/Mn=7.40).

Example 2

Determination of Microbiocidal Activity

Microbiocidal activity is tested according to trivial modifications of the standard EN1040 test method. A bacterial suspension with a cell count of about $10^7$ cfu/m[1] is contacted with appropriate concentrations of the specific substances and the residual cell count is determined after contact time and incubation period. The resulting cell count reduction is compared to a water control.

Specifically, 1 g stock solution with an appropriate concentration of test products are mixed with 8 g water and then inoculated with 1 ml of the selected test organisms. After a given contact period, aliquots are taken, inactivated and diluted. The number of surviving bacteria per ml incubation assay is determined by plate count.

| Test organisms (inoculum) | type |
|---|---|
| *Staphylococcus aureus* ATCC 6538 | Gram-positive bacteria |
| *Escherichia coli* ATCC 10'536 | Gram-negative bacteria |
| *Pseudomonas aeruginosa* ATCC 15442 | Gram-negative bacteria |
| *Candida albicans* ATCC 10'231 | yeast fungi |
| *Aspergillus niger* ATCC 6275 | mould fungi |
| Test concentration: | 10 ppm for bacteria and yeast |
| | 1000 ppm for *A. niger* fungi |
| Contact times: | 5 and 30 minutes at 22° C. |
| Incubation: | 24 h and 7 days at 30° C. |

The test results are shown as log reduction of the initial count in Tables 1 to 4. The data are expressed as measured microorganism concentration (cfu/mL) and log reduction compared to blank ($H_2O$ reference). All polymerized tBAEMA samples tested show good microbicidal activity against bacteria and yeast. The oligomeric or low MW oligomeric tBAEMA sample prepared in Example according to present invention show additional microbial activity against mold fungi *A. niger* with a cell count reduction of 2 logs found after 30 min and 3 logs after 7 days whereas the two higher MW samples of comparative examples did not show any activity after 7 days.

TABLE 1

Test results of microcidal activity against bacteria *S. aureus* (gram-positive) and *E. coli* (gram-negative). Test concentration 10 ppm.

| Sample (10 ppm) | *S. aureus*/ 5 min. | *S. aureus*/ 30 min. | *E. coli*/ 5 min. | *E. coli*/ 30 min. |
|---|---|---|---|---|
| Blank: cfu/mL | $1.52 \times 10^7$ | $1.07 \times 10^7$ | $1.50 \times 10^7$ | $1.49 \times 10^7$ |
| Example 1: MW = 4,500 cfu/mL | $5.18 \times 10^3$ | $<1.0 \times 10^2$ | $1.49 \times 10^6$ | $<1.0 \times 10^2$ |
| log reduction | 3.5 | >5 | 1.0 | >5 |
| Comparative Example A: MW = 174,000 cfu/mL | $1.60 \times 10^4$ | $<1.0 \times 10^2$ | $<1.0 \times 10^2$ | $<1.0 \times 10^2$ |
| log reduction | 3.0 | >5 | >5 | >5 |
| Comparative Example B: MW = 91,000 cfu/mL | $1.04 \times 10^4$ | $<1.0 \times 10^2$ | $<1.0 \times 10^2$ | $<1.0 \times 10^2$ |
| log reduction | 3.2 | >5 | >5 | >5 |

TABLE 2

Test results of microcidal activity against bacteria *Ps. aeruginosa* ATCC 15442 (gram-negative).

| Sample (10 ppm) | 5 min. | 30 min. | 24 h |
|---|---|---|---|
| Blank: cfu/mL | $1.19 \times 10^7$ | $1.16 \times 10^7$ | $2.31 \times 10^7$ |
| Example 1 MW = 4,500 cfu/mL | $3.76 \times 10^5$ | $6.10 \times 10^4$ | $<1.0 \times 10^2$ |
| log reduction | 1.5 | 2.3 | >5 |
| Comparative Example A MW = 174,000 cfu/mL | $1.42 \times 10^3$ | $<1.0 \times 10^2$ | Not tested |
| log reduction | 3.9 | >5 | |
| Comparative Example B MW = 91,000 cfu/mL | $2.44 \times 10^2$ | $<1.0 \times 10^2$ | Not tested |
| log reduction | 3.7 | >5 | |

TABLE 3

Test results of microcidal activity against yeast *C. albicans* ATCC 10'231

| Sample (10 ppm) | 5 min. | 30 min. | 24 h |
|---|---|---|---|
| Blank: cfu/mL | $2.97 \times 10^6$ | $1.81 \times 10^6$ | $3.63 \times 10^6$ |
| Example 1 MW = 4,500 cfu/mL | $3.62 \times 10^4$ | $<1.0 \times 10^2$ | $<1.0 \times 10^2$ |
| log reduction | 1.9 | >4 | >4 |
| Comparative Example A: MW = 174,000 cfu/mL | $7.01 \times 10^3$ | $3.05 \times 10^2$ | $<1.0 \times 10^2$ |
| log reduction | 2.6 | 3.8 | >4 |
| Comparative Example B: MW = 91,000 cfu/mL | $4.17 \times 10^3$ | $1.02 \times 10^2$ | $<1.0 \times 10^2$ |
| log reduction | 2.9 | >4 | >4 |

TABLE 4

Test results of microcidal activity against fungi (molds) *A. niger*

| Sample (1000 ppm) | 30 min. | 1 h | 24 h | 7 days |
|---|---|---|---|---|
| Blank: cfu/mL | $2.90 \times 10^6$ | $1.90 \times 10^6$ | $2.00 \times 10^6$ | $1.90 \times 10^6$ |
| Example 1 MW = 4,500 cfu/mL | $2.50 \times 10^4$ | $1.80 \times 10^4$ | $1.50 \times 10^4$ | $2.10 \times 10^3$ |
| log reduction | 2.1 | 2.0 | 2.0 | 3.0 |
| Comparative Example A: MW = 174,000 cfu/mL | $1.40 \times 10^6$ | $1.20 \times 10^6$ | $1.30 \times 10^6$ | $1.80 \times 10^6$ |
| log reduction | <1 | <1 | <1 | <1 |
| Comparative Example B: MW = 91,000 cfu/mL | $2.30 \times 10^5$ | $2.60 \times 10^5$ | $2.30 \times 10^5$ | $3.20 \times 10^3$ |
| log reduction | 1.1 | <1 | <1 | 2.8 |

Comparative B did not show any activity until 7 days later while Example 1 showed activity (log 2 reduction) in less than 24 h.

Example 3

Antimicrobial Liquid Silicone Rubber Composition Containing Low MW tBAEMA Polymer The liquid silicone rubber (LSR) Med-4960 LSR obtained from NuSil Technology is used in this example. MED-4960 LSR consists of two liquid parts, part A and part B, which must be combined in equal portion prior to use. Part A of Med-4960 contains vinyl terminated polydimthylsiloxane (vinyl-PDMS) and platinum catalyst, and part B contains trimethylsilyl-terminated silicone crosslinker (SiH-PDMS). The antimicrobial polymer can be incorporated in either part or both parts of a LSR formulation. Preferably, the antimicrobial tBAEMA polymer is incorporated in the part containing no metal catalyst such as Part B of Med-4960 from Nusil Technology.

A liquid silicone rubber composition containing antimicrobial tBAEMA homopolymer (Bf) is prepared by dissolving 7.2 g of TBAEMA homopolymer of Example 1 in 10.0 g of THF in a 500 mL flask equipped with agitation and then adding 78.00 g of Med-4960 Part B silicone material to the tBAEMA polymer solution. After complete mixing to homogeneous, the silicone polymer composition is subjected to rotavap at 50° C. in vacuum for 3 hours and additional 24 hrs in a 50° C. vacuum oven to remove THF solvent. The final solvent-free antimicrobial silicone composition (Bf) contains about 8.5% tBAEMA homopolymer of low MW (Mw=5 k).

Similar procedure as described above is followed to prepare silicone composition containing TBAEMA homopolymer of high molecular weight as prepared in Comparison Examples A and B. However, incorporating high MW tBAEMA homopolymer to liquid silicone composition is more difficult as high MW gives a much higher viscosity of the polymer solutions at the same polymer concentration. Therefore, more solvent is needed for the same polymer concentration level to reduce the processing visicosity.

A liquid silicone rubber composition containing antimicrobial tBAEMA homopolymer (Cf1) is prepared by dissolving 6.0 g of TBAEMA homopolymer of Comparison Example B in 26.0 g of THF in a 500 mL flask equipped with agitation and then adding 54.00 g of Med-4960 Part B silicone material to the tBAEMA polymer solution. After complete mixing to homogeneous, the silicone polymer composition is subjected to rotavap at 50° C. in vacuum for 3 hours and additional 24 hrs in a 50° C. vacuum oven to remove THF solvent. The final solvent-free antimicrobial silicone composition (Cf1) contains about 10.0% tBAEMA homopolymer of high MW (Mw=91 k).

A liquid silicone rubber composition containing antimicrobial tBAEMA homopolymer (Cf2) is prepared by dissolving 4.0 g of TBAEMA homopolymer of Comparison Example A in 24.0 g of THF in a 500 mL flask equipped with agitation and then adding 76.00 g of Med-4960 Part B silicone material to the tBAEMA polymer solution. After complete mixing to homogeneous, the silicone polymer composition is subjected to rotavap at 50° C. in vacuum for 3 hours and additional 24 hrs in a 50° C. vacuum oven to remove THF solvent. The final solvent-free antimicrobial silicone composition (Cf1) contains about 5.0% tBAEMA homopolymer of high MW (Mw=174 k).

Example 4

Cured Liquid Silicone Rubber Containing Low MW TBAEMA Polymer by Compress Molding For preparing LSR containing 4% tBAEMA polymer, 45.0 g of antimicrobial silicone composition Bf prepared in Example 3 is mixed with 49.8 g of Med-4960 Part A in a SpeedMixer at 3000 rpm for 2 minutes. The mixed LSR composition was compressed molded at 165° C. for 6 minute. Properly cured solid silicone rubber sheet of 0.04" thickness containing 4% tBAEMA homopolymer is obtained (Example 4A).

Liquid Silicon rubber composition containing different concentration of antimicrobial tBAEMA polymer (see Table Ex4) are prepared by mixing required amount of Bf prepared in Example 3 with Med-4960 Part B and Med-4960 Part A so as to achieve 1:1 ratio of total Part B (including that in Bf) to Part A of Med-4960. Cured silicone rubber sheets of 0.04" thickness are obtained by compress molding of the LSR composition at 165° C. for 6 minutes.

Blank silicone rubber sheets without the antimicrobial tBAEMA polymer are also prepared for comparison by mixing equal amount 50 g each of Part A and Part B of the Med-4960 LSR and compress molded at 165° C. for 3 minute.

TABLE EX4

Liquid Silicon Rubber (LSR) composition containing different concentration of antimicrobial tBAEMA polymer

| Example | Antimicrobial LSR of Example 3 | Med-4960 Part B | Med-4960 Part A | tBAEMA polymer content | reference |
|---|---|---|---|---|---|
| 4A | 45.0 (Bf) | 0 | 49.8 | 4% | 16zs252C |
| 4B | 23.5 (Bf) | 26.5 | 48.8 | 2% | 16zs252D |
| 4C | 11.8 (Bf) | 38.2 | 50.0 | 1% | 16zs274B |
| 4D | 5.9 (Bf) | 44.1 | 50.0 | 0.5% | 16zs274C |
| 4E | 42.2 (Cf1) | 7.8 | 46.1 | 4% | 16zs253C |
| 4F | 40.0 (Cf2) | 10.0 | 50.0 | 2% | 16zs252D |
| 4G | 20.0 (Cf2) | 30.0 | 50.0 | 1% | 16zs274B |
| 4H | 10.0 (Cf2) | 40.0 | 50.0 | 0.5% | 16zs274C |

Example 5

Determination of Microbicidal Activity

The silicone rubber sheets prepared in Example 4 was cut into 2 cm×2 cm square coupons for testing.

Microbicidal surface activity of the antimicrobial silicone rubber is tested according JIS Z2801 standard test method.

| Test strain: | *Escherichia coli* | ATCC 10536 (E.c. 27) |
|---|---|---|
| | *Staphylococcus aureus* | ATCC 6538 (S.a. 16) |

Silicone rubber containing no antimicrobial polymer is tested as blank control and used as a base for calculation of the log reduction of the microorganism after the microbicidal activity testing. The results after 24 h of contact time are summarized in Table EX5 showing log reduction against gram negative (*E. coli*) and gram positive (*S. aureus*) bacteria. Both high and low MW tBAEMA polymers showed great activity against *S. aureus* and *E. coli* bacteria at high 4% level. The low MW (5 k) tBAEMA continued to show activity at concentration as low as 1% while the high MW (170 k) did not show activity up to 2% concentration. Thus, the low MW tBAEMA is more efficient with the silicone rubber substrate. This example demonstrates the advantage of the low MW tBAEMA homopolymer of the present invention over high MW tTBAEMA hompolymer for more efficient antimicrobial activity in non polar substrates such silicone rubber.

TABLE EX5

Microcidal activity against bacteria (JIS Z 2801 test method, contact time 24 h)

| Silicone rubber Example | TBAEMA polymer | *E. coli* [log-reduction] | *S. aureus* [log-reduction] |
|---|---|---|---|
| 4A | Low MW (5k) pTBAEMA (4%) | >4.0 | >4.0 |
| 4B | Low MW (5k) pTBAEMA (2%) | 3.7 | >4.0 |
| 4C | Low MW (5k) pTBAEMA (1%) | <1 | >4.0 |
| 4D | Low MW (5k) pTBAEMA (0.5%) | <1 | <1 |
| 4E | Medium MW (91k) pTBAEMA (4%) | >4.0 | >4.0 |
| 4F | High MW (170k) pTBAEMA (2%) | 1.5 | <1 |
| 4G | High MW (170k) pTBAEMA (1%) | <1 | <1 |
| 4H | High MW (170k) pTBAEMA (0.5%) | <1 | <1 |

Example 6

Agar Diffusion Assay (CLSI M02-A10) to Check Leachable Antimicrobials

Agar diffusion assay (CLSI M02-A10) is carried out on the antimicrobial silicone rubber prepared in Example 4 to evaluate leachablity of the antimicrobial tBAEMA homopolymer from the substrate. Results of the agar diffusion assay are summarized in Table Ex5. None of the silicone rubber samples showed an inhibition zone.

TABLE EX5

Summary of agar diffusion assay results

| Silicone rubber Example | TBAEMA polymer | *E. coli* ATCC 10536 Diameter [cm] | *S. aureus* ATCC 6538 Diameter [cm] |
|---|---|---|---|
| Control | (blank silicone rubber) | No zone of inhibiton Diameter: 0 cm | No zone of inhibiton Diameter: 0 cm |
| 4A | Low MW (5k) pTBAEMA (4%) | No zone of inhibiton Diameter: 0 cm | No zone of inhibiton Diameter: 0 cm |
| 4B | Low MW (5k) pTBAEMA (2%) | No zone of inhibiton Diameter: 0 cm | No zone of inhibiton Diameter: 0 cm |

TABLE EX5-continued

Summary of agar diffusion assay results

| Silicone rubber Example | TBAEMA polymer | E. coli ATCC 10536 Diameter [cm] | S. aureus ATCC 6538 Diameter [cm] |
|---|---|---|---|
| 4E | Medium MW (91k) pTBAEMA (4%) | No zone of inhibiton Diameter: 0 cm | No zone of inhibiton Diameter: 0 cm |

The results of Example 5 and Example 6 together demonstrate that tBAEMA homopolymer is a nonleachable antimicrobial. In application to silicone rubber, the low MW TBAEMA homopolymer of present invention gives more efficient antimicrobial activity at a lower dosage than the high MW ones. The low MW tBAEMA homopolymer is also a non-leachable antimicrobial and thus capable of providing a permanent antimicrobial surface.

GPC method for determination of molecular weights:
GPC Column: Waters Ultrastyragel Linear
Detector: Refractive Index
Column temperature: ambient
Mobile phase: THF (HPLC grade) containing 1.1% diethanolamine
Elution rate: 0.5 mL/min
Injection volume: 100 μL
Run time: 30 min
MW Standards: EasyVial PMMA (PolymerLabs)

Example 7

Antimicrobial Poly(Vinyl Chloride) (PVC) Coatings Containing Low MW tBAEMA Polymer (16zs257A)

A). 9.5 g of poly(vinyl chloride) (PVC) powder (inherent viscosity 0.68) purchased from Aldrich Chemicals and 0.5 g of pTBAEMA prepared in Example 1 are dissolved in 145 g of THF solvent under agitation to give a solution for PVC coating containing 5% of low MW pTBAEMA of the present invention.
B). 9.5 g of poly(vinyl chloride) (PVC) powder (inherent viscosity 0.68) purchased from Aldrich Chemicals and 0.5 g of pTBAEMA prepared in comparision Example A are dissolved in 145 g of THF solvent under agitation to give a solution for PVC coating containing 5% of high MW pTBAEMA as comparison example.
C). 10.0 g of poly(vinyl chloride) (PVC) powder (inherent viscosity 0.68) purchased from Aldrich Chemicals is dissolved in 145 g of THF solvent under agitation to give a solution as for blank PVC coatings as control.

| Example | 7A | 7B | 7C |
|---|---|---|---|
| tBAEMA polymer used | Example 1 | Comparison Example A | none |
| tBAEMA polymer content | 5% | 5% | 0% |

About 6 g of PVC polymer solutions, A, B and C, are cast on Teflon dishes of 6 cm diameter and allow drying at room temperature overnight. The dry PVC coating as film circles with 6 cm diameter are peeled off from the Teflon dishes for evaluation.

The PVC coating films (7A and 7B) containing 5% TBAEMA homopolymers were tested using JIS Z 2801 method against E. coli and S. Aureus. PVC coating film (7C) containing no antimicrobial polymer is tested as blank control and used as a base for calculation of the log reduction of the microorganism after the microbicidal activity testing. The results after 24 h of contact time are summarized in Table EX7 showing log reduction against gram negative (E. coli) and gram positive (S. aureus) bacteria. Both high and low MW tBAEMA polymers showed great activity against S. aureus and E. coli bacteria at high 5% level.

TABLE EX7

Microcidal activity against bacteria (JIS Z 2801 test method, contact time 24 h)

| PVC coating Example | tBAEMA polymer | E. coli [log-reduction] | S. aureus [log-reduction] |
|---|---|---|---|
| 7A | Low MW (5k) pTBAEMA (5%) | >5.7 | >5.5 |
| 7B | High MW (170k) pTBAEMA (5%) | >5.7 | >5.5 |

The PVC films were observed with an optical microscope to see possible phase separation and surface morphology of the polytBAEMA incorporated samples in comparison with the blank PVC coating film prepared in the same conditions. The low MW pTBAEMA incorporated PVC film (7A) showed homogeneous morphology similar to that of the blank PVC (7C) while the high MW polytBAEMA incorporated PVC film (7B) showed some inhomogeneous aggregates on the surface. (FIG. 1 for Example 7). This demonstrates benefit of the low MW polytBAEMA of the present invention in comparison with PVC to give films of better quality than the high MW one. Less phase separation of PVC containing tBAEMA oligomer of the present invention can lead to materials with enhanced mechanical properties.

Example 8a

Preparation of tBAEMA Homopolymers by Conventional Radical Polymerization Process 480 g of tetrahydrofuran (THF) solvent are charged to a 1 L reactor equipped with overhead condenser and agitator. The reactor content with overhead condenser is heated to 65° C. under agitation and nitrogen sparging for 1 hour. After 1 hour nitrogen sparging and the reaction temperature reaches 65° C., 120 g of t-butylaminoethyl methacrylate (tBAEMA) monomer (M) and an initiator solution (I) comprising 10 g of AIBN (azobisisobutyronitrile) and 100 g of THF are added to the reactor slowly over about 180 minutes. The reactor is maintained at reflux temperature under nitrogen blanket and agitation during the (I) feed and for additional 3 hours after the feeds. The reactor content is cooled down to room temperature. The reactor content is precipitated in 2 L of heptane. The polymer product is removed by filtration, washed with 500 mL of fresh heptane and dried in a vacuum oven at 50° C. for overnight. The polymer product is analyzed with gel permeation chromatography (GPC) to have a number average molecular weight (Mn) of 4,500 g/mole and a weight average molecular weight (Mw) of 11,000 g/mole using poly(methyl methacrylate) monodisperse molecular weight standards from Polymer Labs. The molecular weight polydispersity index (PDI=Mw/Mn) is 2.47.

Example 8b

Preparation of tBAEMA Homopolymers by Conventional Radical Polymerization Process 480 g of tetrahydrofuran (THF) solvent are charged to a 1 L reactor equipped with overhead condenser and agitator. The reactor content with overhead condenser is heated to 65° C. under agitation and nitrogen sparging for 1 hour. After 1 hour nitrogen sparging and the reaction temperature reaches 65° C., 120 g of t-butylaminoethyl methacrylate (tBAEMA) monomer (M) and an initiator solution (I) comprising 6 g of AIBN (azobisisobutyronitrile) and 60 g of THF are added to the reactor slowly over about 60 minutes. The reactor is maintained at reflux temperature under nitrogen blanket and agitation during the (I) feed and for additional 3 hours after the feeds. The reactor content is cooled down to room temperature. The reactor content is precipitated in 2 L of heptane. The polymer product is removed by filtration, washed with 500 mL of fresh heptane and dried in a vacuum oven at 50° C. for overnight. The polymer product is analyzed with gel permeation chromatography (GPC) to have a number average molecular weight (Mn) of 13,400 g/mole and a weight average molecular weight (Mw) of 37,500 g/mole using poly (methyl methacrylate) monodisperse molecular weight standards from Polymer Labs. The molecular weight polydispersity index (PDI=Mw/Mn) is 2.80.

Example 8c

Preparation of tBAEMA Homopolymers by Conventional Radical Polymerization Process 160 g of tetrahydrofuran (THF) solvent and 40 g of t-butylaminoethyl methacrylate (tBAEMA) monomer (M) are charged to a 1 L reactor equipped with overhead condenser and agitator. The reactor content with overhead condenser is heated to 65° C. under agitation and nitrogen sparging for 1 hour. After 1 hour nitrogen sparging and the reaction temperature reaches 65° C., an initiator solution (I) comprising 0.4 g of AIBN (azobisisobutyronitrile) and 40 g of THF are added to the reactor slowly over about 60 minutes. The reactor is maintained at reflux temperature under nitrogen blanket and agitation during the (I) feed and for additional 3 hours after the feeds. The reactor content is cooled down to room temperature. The reactor content is precipitated in 1 L of heptane. The polymer product is removed by filtration, washed with 300 mL of fresh heptane and dried in a vacuum oven at 50° C. for overnight. The polymer product is analyzed with gel permeation chromatography (GPC) to have a number average molecular weight (Mn) of 54,500 g/mole and a weight average molecular weight (Mw) of 135,000 g/mole using poly(methyl methacrylate) monodisperse molecular weight standards from Polymer Labs. The molecular weight polydispersity index (PDI=Mw/Mn) is 2.62

Example 9

Antimicrobial Thermoplastic Urethane (TPU) Containing tBAEMA Polymer

Thermoplastic urethane (TPU) (Elastollan 1190A) from BASF is used as matrix polymer. TPU blend containing antimicrobial TBAEMA polymer is obtained by melt extrusion compounding in a twin screw extruder with temperature setting from 195 to 205° C. and pelletized. TPU plaques (25×25 cm$^2$) of 1.5 mm thickness are prepared by compression molding of the TPU pellets at 200° C. and used for evaluation of biocidal activity. The TPU plaques containing 2% tBAEMA homopolymer of three different Mw prepared in Example 7a are tested using JIS Z 2801 method against *E. coli* and *S. Aureus*. Results shown in Table Ex9 clearly demonstrate increased bioactivity with decreasing Mw. The TPU with the lowest Mw (11 k) polytBAEMA gives full bioactivity (>5 log reduction) against both tested microoganisms while the one with the highest Mw (135 k) polytBAEMA gives activity only moderate (3.1 log reduction) against *S. aureus* and a little (1.2 log reduction) against *E. coli*. The TPU with medium Mw (37.5 k) has the bioactivity performance in between showing full activity (>5 log reduction) against *S. aureus* but only moderate activity (2.4 log reduction) against *E. coli*.

TABLE EX 9

Microcidal activity of TPU samples containing 2% pTBAEMA against bacteria (JIS Z 2801 test method, contact time 24 h)

| polytBAEMA material used | *E. coli* [log-reduction] | *S. aureus* [log-reduction] |
| --- | --- | --- |
| Example 8a (Mw = 11.0k) | 5.2 | 5.2 |
| Example 8b (Mw = 37.5k) | 2.4 | 5.2 |
| Example 8c (Mw = 135k) | 1.2 | 3.1 |

FIG. 2 for Example 9 shows a photograph of three TPU blend plaques containing 2% polytBAEMA of different Mw. The TPU with the low Mw (11 k) is the most transparent similar to that of blank control (not shown). The TPU with the highest Mw has more rough morphology and tends to be more opaque indicating less compatibility of the high Mw polytBAEMA with matrix TPU. The TPU with medium Mw shows medium transparency in comparison. Less phase separation of TPU containing tBAEMA oligomer of the present invention lead to materials with enhanced bioactivity and mechanical properties.

Example 10

Preparation of Low MW tBAEMA Homopolymer with Narrow Molecular Weight Distribution by Conventional Radical Polymerization Process 4800 g of tetrahydrofuran (THF) solvent is charged to a 10 L reactor equipped with overhead condenser and agitator. The reactor content with overhead condenser is heated to 65° C. under agitation and nitrogen sparging for 1 hour. After 1 hour nitrogen sparging and the reaction temperature reaches 65° C., 1200 g of t-butylaminoethyl methacrylate (tBAEMA) monomer (M) and an initiator solution (I) comprising 150 g of AIBN (azobisisobutyronitrile) and 1500 g of THF are added to the reactor slowly over about 180 minutes. The reactor is maintained at reflux temperature under nitrogen blanket and agitation during the M and I feeds and for additional 3 hours after the feeds. Monomer conversion is more than 95% after the polymerization reaction. The reactor content is heated to distill out about 5000 g of solvent. Fresh THF solvent (2000 g) is added to the reactor and distillation of solvent out of the reactor is repeated until residual monomer is less than 1%. The reactor content is cooled down to room temperature. The final solution polymer product contains 75% polymer solids. The polymer product is analyzed with gel permeation chromatography (GPC) to have a number average molecular weight (Mn) of 2,850 g/mole and a weight average molecular weight (Mw) of 6,900 g/mole using poly(methyl methacrylate) monodisperse molecular weight standards from Polymer Labs. The molecular weight polydispersity index (PDI=Mw/Mn) is 2.42.

Example 11

The homopolymer made according to example 8a, Mw 11,000 was tested for activity on *Malassezia furfur* (dandruff causing organism).

Experiments were carried out in quadruplicates for each sample.

The homopolymer is added to a shampoo formulation, culture media and cell culture, mixed and incubated for three minutes at 40° C. before plating. A comparison is made on the number of colonies per plate. A lower number indicates effectiveness against *M. furfur*.

TABLE 11

Activity of inventive polymer against *M. furfur*

| Trial | Sample | Concentration of polymer in shampoo | Amount of colonies/per plate |
|---|---|---|---|
| 1 | Shampoo + water | — | 270 |
|  | Shampoo + polymer | 0.2 | 50 |
|  |  | 0.1 | ~10 |
|  |  | 0.05 | ~20 |
|  | 20% Ethanol + water |  | 250 |
|  | 10% Ethanol |  | 250 |
|  | Water (control) |  | 375 |
| 2 | Shampoo + water |  | 275 |
|  | Shampoo + polymer | 0.2 | 10 |
|  |  | 0.1 | 5 |
|  |  | 0.05 | 12 |
|  | 20% Ethanol |  | 245 |
|  | 10% Ethanol |  | 260 |
|  | Water (control) |  | 375 |

Example 12

The inventive polymer is tested on air filtration media from FiberVision.

Sample preparation: nonwovens were cut into pieces of 2×2 cm

Test method: CG 190/modified AATCC-100

CG 190: Toxicity & inactivation control according to EN1040

Test organisms: *Klebsiella pneumoniae* DSM 789
*Staphylococcus aureus* DSM 799 (~) ATCC 10536

The media is a nonwoven made from PE sheath/PET core bicomponent fibers and has a weight of 11 g/m². The samples were treated by saturating in solutions containing the antimicrobial polymer without binder. The loading was adjusted by changing the concentration. After saturation, the excess was allowed to drain off the sample and then the sample was oven dried. The loading level was determined by measuring the weight change of the sample.

TABLE 12a

Results cfu/samples and log reductions compared to blank control (24 h) on Air Filtration Media

| Sample ID | Binder/ Loading | Antimicrobial/ Loading | K. pneumoniae DSM 789 [cfu/sample] | S. aureus DSM 799 [cfu/sample] | K. pneumoniae DSM 789 [log-reduction] | S. aureus DSM 799 [log-reduction] |
|---|---|---|---|---|---|---|
|  |  | Blank 0 h | 2.3E+05 | 2.2E+05 |  |  |
|  |  | Blank 24 h | 6.0E+07 | 4.4E+07 | 5.6E+07 | 4.8E+07 |
|  |  |  | 5.1E+07 | 5.0E+07 |  |  |
| 1 | None | Poly tBAEMA[1]/ 2.7% | <100 | <100 | >5.7 | >5.7 |
|  |  |  | <100 | <100 | >5.7 | >5.7 |
| 2 | None | Poly tBAEMA/ 3.2% | <100 | <100 | >5.7 | >5.7 |
|  |  |  | <100 | <100 | >5.7 | >5.7 |

[1] Poly tBAEMA according to example 10 and Mw of 7,000.

Results table 12b:

Toxicity controls and inactivation (CG 190)

Results cfu/samples and recovery rates compared to blank control (30 min)

Inactivation media: phosphate buffer with 1% Tween 80 and 0.3% soy lecithin

| Sample ID | Binder/ Loading | Antimicrobial/ Loading | K. pneumoniae DSM 789 [cfu/sample] | S. aureus DSM 799 [cfu/sample] | K. pneumoniae DSM 789 [recovery rate %] | S. aureus DSM 799 [recovery rate %] |
|---|---|---|---|---|---|---|
|  |  | Blank 0 h | 1.2E+08 | 1.1E+08 |  |  |
|  |  | Blank 24 h | 1.0E+08 | 8.9E+07 | 9.7E+07 | 1.0E+08 |
|  |  |  | 9.4E+07 | 1.1E+08 |  |  |
| 2 | none | Poly tBAEMA/ 3.2% | 1.3E+08 | 8.8E+07 | 134 | 88 |
|  |  |  | 1.1E+08 | 8.6E+07 | 113 | 86 |

Example 13

A one-component acrylic thermoset clearcoat based on an acrylic carbamate crosslinked with an alkoxylated melamine is used as the polymer coating system which are incorporated the antimicrobial oligomers according to example 10.

| Formulation | Additive | Bake Temperature | Bake Time | Hardness (KHN) |
|---|---|---|---|---|
| A | None | 140° C. | 30 minutes | 18 |
| B | 2% pTBAEMA | 160° C. | 30 minutes | 11 |
| C | 5% pTBAEMA | 160° C. | 30 minutes | 16 |

The bake times and temperatures were designed to achieve complete cure, as indicated by Knoop indentation hardness values.

All percentages are based on active additive and coating polymer solids.

The molecular weight of pTBAEMA is Mw=6930; Mw/Mn=2.85 according to example 10.

Each coating formulation is applied by spin coating onto transparent glass slides approximately 2"×2" to a film thickness of about 14-18 microns dry film thickness. Twelve replicate slides of each formulation are produced.

Two slides of each formulation, plus triplicate blank glass slides controls are subjected to antimicrobial activity evaluation via the JIS Z2801 industry standard, against *E. coli* bacteria using a 24 hour incubation period. The same number of replicates and controls are evaluated via the same method vs *S. aureus* bacteria using a 24 hour incubation and a 5 hour incubation.

The results of antimicrobial testing may be expressed as $\log_{10}$ reduction of colony forming units (DFU's) vs the blank glass slide control. These results are as follows:

| Formulation | Additive | $\log_{10}$ reduction vs *E. coli* 24 hours | $\log_{10}$ reduction vs *S. aureus* 5 hours | $\log_{10}$ reduction vs *S. aureus* 24 hours |
|---|---|---|---|---|
| Glass Control | | — | — | — |
| A | None | 0.08 | −0.17 | .04 |
| B | 2% pTBAEMA | 5.7 | 2.4 | 3.4 |
| C | 5% pTBAEMA | 5.7 | 3.4 | 5.8 |

We claim:

1. An antimicrobial composition comprising a material selected from the group consisting of coatings, inks, adhesives, lubricants, textiles, polymers, plastics, rubbers, waxes, ceramics, metals, glass, superabsorbers, membranes, gels, wood or cellulosic substrates, paper, pharmaceuticals, water, home and personal care formulations, packaging materials and cosmetics which material is treated with or is mixed with an antimicrobial homo-oligomer-formed from 2-tert-butylaminoethyl methacrylate (tBAEMA) only and the homo-oligomer has a weight average molecular weight (Mw) of 400 to 20,000 g/mole, optionally with a polydispersity index between 1 and 4.0 (determined according to GPC using poly (methyl methacrylate) narrow Mw standards), wherein the homo-oligomer does not form a block.

2. The antimicrobial composition according to claim 1 wherein the homo-oligomer is represented by formula (II)

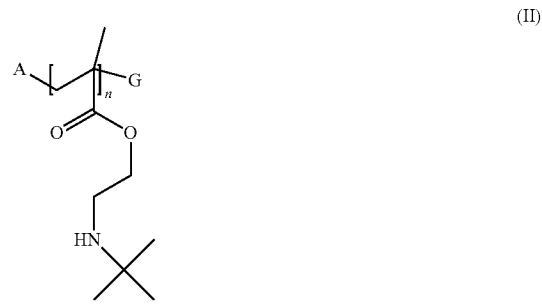

(II)

where n is from 2 to 100 and A and G are residual groups derived from a polymerization initiator and optionally a chain transfer agent.

3. The antimicrobial composition according to claim 2, wherein A and G are derived from polymerization initiators selected from the group consisting of free radical polymerization initiators, atom transfer radical polymerization (ATRP) initiators, nitroxide-mediated radical polymerization (NMP) initiators, reversible addition-fragmentation chain transfer polymerization (RAFT) or macromolecular design via interchange of xanthates (MADIX).

4. The antimicrobial composition according to claim 3, wherein the polymerization initiator is a free radical polymerization initiator with A and G being derived from the residual group of initiators selected from the group consisting of azo and peroxide initiators and optionally a chain transfer agent.

5. The antimicrobial composition according to claim 4, wherein the initiator is an atom transfer radical polymerization initiator and G is a halogen.

6. The antimicrobial composition according to claim 1, wherein the material is a polymer.

7. The antimicrobial composition according to claim 6, wherein the polymer is selected from the group consisting of polysiloxane, silicon rubber, polyolefins, polyvinylchloride, polymethylmethacrylate, polyesters, polytetrafluoroethylene, polyamides, natural rubbers, polyacetal, polysulfones, polyurethanes, polyethers and polycarbonates.

8. A process of imparting antimicrobial and odor reducing properties to a material comprising the steps of incorporating the oligomer according to claim 1 into or treating said material, wherein the material is selected from the group consisting of coatings, inks, adhesives, lubricants, gels, textiles, membranes, polymers, plastics, waxes, metals, ceramics, wood or cellulosic substrates, superabsorbers, rubbers, paper, pharmaceuticals, water, home or personal care formulations, packaging material and cosmetics.

9. A process of forming an antimicrobial silicone rubber composition, comprising the steps of
   i.) adding the oligomer according to claim 1
   to a silicone rubber composition which composition comprises
      a polysiloxane,
      optionally a crosslinker and/or filler, and
      a catalyst,
   ii.) and curing.

10. A method of forming an antimicrobial oligomer according to claim 1, wherein tBAEMA is polymerized by free radical polymerization with an azo compound as a radical initiator and the polymerization process comprises cofeeding tBAEMA and an azo compound wherein the molar ratio of tBAEMA to azo compound ranges from 20:1 to 5:1.

11. An antimicrobial homo-oligomer of formula (II)

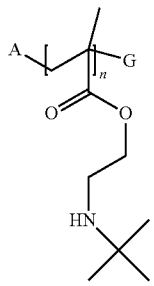

(II)

where n is from 2 to 100 and A and G are residual groups derived from an initiator and optionally a chain transfer agent,
wherein the mole percent of A+G
ranges from about 1 to about 30 mole percent based on the total moles of A+G and monomer units and the initiator is a free radical initiator selected from the group consisting of azo and peroxide initiators.

12. The antimicrobial oligomer of formula (II) according to claim 11, wherein the antimicrobial oligomer is characterized by a $T_g$ of $=<30°$ C.

13. The antimicrobial composition according to claim 1, which material is treated with or mixed with 0.1 to about 5 wt. % of the antimicrobial homo-oligomer formed from 2-tert-butylaminoethyl(methacrylate) and the wt. % is based on the total weight of the material.

14. The antimicrobial composition according to claim 1, wherein the material is a textile and the textile is a non-woven.

15. The antimicrobial composition according to claim 1, wherein the material is a coating.

16. The antimicrobial composition according to claim 1, wherein the material is a home or personal care formulation and the home care formulation is selected from the group consisting of household and general-purpose cleaners for cleaning and disinfecting hard surfaces and the personal care formulation is selected from the group consisting of shampoos, bath additives, hair care preparations, liquid and solid soaps, lotions and creams, deodorants, cleansing solutions for the skin and moist cleaning cloths.

17. The antimicrobial composition according to claim 1, wherein the material is a cosmetic.

* * * * *